United States Patent
Levinson et al.

(10) Patent No.: US 12,070,411 B2
(45) Date of Patent: Aug. 27, 2024

(54) CRYOPROTECTANT FOR USE WITH A TREATMENT DEVICE FOR IMPROVED COOLING OF SUBCUTANEOUS LIPID-RICH CELLS

(71) Applicant: Zeltiq Aesthetics, Inc., Pleasanton, CA (US)

(72) Inventors: Mitchell E. Levinson, Pleasanton, CA (US); Donald Johnson, Danville, CA (US); Jessica Preciado, Alameda, CA (US); Edward A. Ebbers, San Carlos, CA (US); Daniel Bucks, Millbrae, CA (US)

(73) Assignee: Zeltiq Aesthetics, Inc., North Chicago, IL (US)

( * ) Notice: Subject to any disclaimer, the term of this patent is extended or adjusted under 35 U.S.C. 154(b) by 0 days.

(21) Appl. No.: 16/595,466

(22) Filed: Oct. 8, 2019

(65) Prior Publication Data

US 2020/0155215 A1    May 21, 2020

Related U.S. Application Data

(63) Continuation of application No. 13/747,161, filed on Jan. 22, 2013, now abandoned, which is a
(Continued)

(51) Int. Cl.
*A61F 7/00*    (2006.01)
*A61B 18/00*    (2006.01)
(Continued)

(52) U.S. Cl.
CPC ............... *A61F 7/00* (2013.01); *A61B 18/02* (2013.01); *A61B 18/12* (2013.01); *A61B 18/203* (2013.01);
(Continued)

(58) Field of Classification Search
CPC ............................................. A61F 2007/0075
See application file for complete search history.

(56) References Cited

U.S. PATENT DOCUMENTS

| | | |
|---|---|---|
| 681,806 A | 9/1901 | Mignault et al. |
| 889,810 A | 6/1908 | Robinson et al. |
| (Continued) | | |

FOREIGN PATENT DOCUMENTS

| | | |
|---|---|---|
| AU | 2011253768 A1 | 6/2012 |
| CA | 2441489 A1 | 3/2005 |
| (Continued) | | |

OTHER PUBLICATIONS

Aguilar et al., "Modeling Cryogenic Spray Temperature and Evaporation Rate Based on Single-Droplet Analysis," Eighth International Conference on Liquid Atomization and Spray Systems, Pasadena, CA, USA, Jul. 2000, 7 pages.
(Continued)

*Primary Examiner* — Kaitlyn E Smith

(57) ABSTRACT

A cryoprotectant for use with a treatment device for improved removal of heat from subcutaneous lipid-rich cells of a subject having skin is provided. The cryoprotectant is a non-freezing liquid, gel, or paste for allowing pre-cooling of the treatment device below 0° C. while preventing the formation of ice thereon. The cryoprotectant may also prevent freezing of the treatment device to the skin or ice from forming from moisture seeping out from the skin. The cryoprotectant may further be hygroscopic, thermally conductive, and biocompatible.

24 Claims, 11 Drawing Sheets

Related U.S. Application Data continuation of application No. 11/741,271, filed on Apr. 27, 2007, now abandoned.

(60) Provisional application No. 60/795,799, filed on Apr. 28, 2006.

(51) Int. Cl.
  *A61B 18/02* (2006.01)
  *A61B 18/12* (2006.01)
  *A61B 18/20* (2006.01)
  *A61F 7/02* (2006.01)
  *A61F 7/10* (2006.01)
  *A61B 90/00* (2016.01)

(52) U.S. Cl.
  CPC ...... *A61F 7/10* (2013.01); *A61B 2018/00047* (2013.01); *A61B 2018/00101* (2013.01); *A61B 2018/00107* (2013.01); *A61B 2018/00464* (2013.01); *A61B 2018/00642* (2013.01); *A61B 2018/00714* (2013.01); *A61B 2018/00744* (2013.01); *A61B 2018/00791* (2013.01); *A61B 2018/0231* (2013.01); *A61B 90/04* (2016.02); *A61F 2007/0001* (2013.01); *A61F 2007/0075* (2013.01); *A61F 2007/0219* (2013.01); *A61F 2007/0246* (2013.01); *A61F 2007/029* (2013.01)

(56) References Cited

U.S. PATENT DOCUMENTS

| | | | |
|---|---|---|---|
| 1,093,868 | A | 4/1914 | Leighty |
| 2,516,491 | A * | 7/1950 | Swastek ............... A61H 7/003 401/28 |
| 2,521,780 | A | 9/1950 | Dodd et al. |
| 2,726,658 | A | 12/1955 | Chessey |
| 2,766,619 | A | 10/1956 | Tribus et al. |
| 2,851,602 | A | 9/1958 | Cramwinckel et al. |
| 3,093,135 | A | 6/1963 | Hirschhorn |
| 3,132,688 | A | 5/1964 | Nowak |
| 3,133,539 | A | 5/1964 | William et al. |
| 3,282,267 | A | 11/1966 | Eidus |
| 3,341,230 | A | 9/1967 | Louis |
| 3,502,080 | A | 3/1970 | Hirschhorn |
| 3,566,871 | A | 3/1971 | Richter et al. |
| 3,587,577 | A | 6/1971 | Zubkov et al. |
| 3,591,645 | A | 7/1971 | Selwitz |
| 3,692,338 | A | 9/1972 | Didier |
| 3,702,114 | A | 11/1972 | Zacarian |
| 3,703,897 | A | 11/1972 | Mack et al. |
| 3,710,784 | A | 1/1973 | Taylor |
| 3,786,814 | A | 1/1974 | Armao |
| 3,827,436 | A | 8/1974 | Andera et al. |
| 3,942,519 | A | 3/1976 | Shock |
| 3,948,269 | A | 4/1976 | Zimmer |
| 3,986,385 | A | 10/1976 | Johnston et al. |
| 3,993,053 | A | 11/1976 | Grossan |
| 4,002,221 | A | 1/1977 | Buchalter |
| 4,008,910 | A | 2/1977 | Roche |
| 4,026,299 | A | 5/1977 | Sauder |
| 4,140,130 | A | 2/1979 | Storm |
| 4,149,529 | A | 4/1979 | Copeland et al. |
| 4,178,429 | A | 12/1979 | Scheffer |
| 4,202,336 | A | 5/1980 | Van Gerven |
| 4,266,043 | A | 5/1981 | Fujii et al. |
| 4,269,068 | A | 5/1981 | Molina |
| D260,173 | S | 8/1981 | Wiebe |
| 4,381,009 | A | 4/1983 | Del Bon |
| 4,396,011 | A | 8/1983 | Mack et al. |
| 4,459,854 | A | 7/1984 | Richardson et al. |
| 4,470,263 | A | 9/1984 | Lehovec et al. |
| 4,483,341 | A | 11/1984 | Witteles |
| 4,528,979 | A | 7/1985 | Marchenko et al. |
| 4,531,524 | A | 7/1985 | Mioduski |
| 4,548,212 | A | 10/1985 | Leung |
| 4,555,313 | A | 11/1985 | Duchane et al. |
| 4,585,002 | A | 4/1986 | Kissin |
| 4,603,076 | A | 7/1986 | Bowditch et al. |
| 4,614,191 | A | 9/1986 | Perler et al. |
| 4,644,955 | A | 2/1987 | Mioduski |
| 4,664,110 | A | 5/1987 | Schanzlin |
| 4,700,701 | A | 10/1987 | Montaldi |
| 4,718,429 | A | 1/1988 | Smidt |
| 4,741,338 | A | 5/1988 | Miyamae |
| 4,758,217 | A | 7/1988 | Gueret |
| 4,764,463 | A * | 8/1988 | Mason ............... A01N 1/0221 424/532 |
| 4,802,475 | A | 2/1989 | Weshahy |
| 4,832,022 | A | 5/1989 | Tjulkov et al. |
| 4,841,969 | A | 6/1989 | Donnerhack et al. |
| 4,846,176 | A | 7/1989 | Golden |
| 4,850,340 | A | 7/1989 | Onishi |
| 4,869,250 | A | 9/1989 | Bitterly |
| 4,880,564 | A | 11/1989 | Abel et al. |
| 4,905,697 | A | 3/1990 | Heggs et al. |
| 4,906,463 | A | 3/1990 | Cleary et al. |
| 4,930,317 | A | 6/1990 | Klein |
| 4,935,345 | A | 6/1990 | Guilbeau et al. |
| 4,961,422 | A | 10/1990 | Marchosky et al. |
| 4,962,761 | A | 10/1990 | Golden |
| 4,990,144 | A | 2/1991 | Blott et al. |
| 5,007,433 | A | 4/1991 | Hermsdoerffer et al. |
| 5,018,521 | A | 5/1991 | Campbell et al. |
| 5,024,650 | A | 6/1991 | Hagiwara et al. |
| 5,065,752 | A | 11/1991 | Sessions et al. |
| 5,069,208 | A | 12/1991 | Noppel et al. |
| 5,084,671 | A | 1/1992 | Miyata et al. |
| 5,108,390 | A | 4/1992 | Potocky et al. |
| 5,119,674 | A | 6/1992 | Nielsen |
| 5,139,496 | A | 8/1992 | Hed |
| 5,143,063 | A | 9/1992 | Fellner |
| 5,148,804 | A | 9/1992 | Hill et al. |
| 5,158,070 | A | 10/1992 | Dory |
| 5,160,312 | A | 11/1992 | Voelkel |
| 5,169,384 | A | 12/1992 | Bosniak et al. |
| 5,197,466 | A | 3/1993 | Marchosky et al. |
| 5,207,674 | A | 5/1993 | Hamilton |
| 5,209,227 | A | 5/1993 | Deutsch |
| 5,221,726 | A | 6/1993 | Dabi et al. |
| 5,264,234 | A | 11/1993 | Windhab et al. |
| 5,277,030 | A | 1/1994 | Miller |
| 5,288,469 | A | 2/1994 | Skalla |
| 5,314,423 | A | 5/1994 | Seney et al. |
| 5,327,886 | A | 7/1994 | Chiu |
| 5,330,745 | A | 7/1994 | Mcdow et al. |
| 5,333,460 | A | 8/1994 | Lewis et al. |
| 5,334,131 | A | 8/1994 | Omandam et al. |
| 5,336,616 | A | 8/1994 | Livesey et al. |
| 5,339,541 | A | 8/1994 | Owens |
| 5,342,617 | A | 8/1994 | Gold et al. |
| 5,351,677 | A | 10/1994 | Kami et al. |
| 5,358,467 | A | 10/1994 | Milstein et al. |
| 5,362,966 | A | 11/1994 | Rosenthal et al. |
| 5,363,347 | A | 11/1994 | Nguyen |
| 5,372,608 | A | 12/1994 | Johnson |
| 5,386,837 | A | 2/1995 | Sterzer |
| 5,411,541 | A | 5/1995 | Bell et al. |
| 5,427,772 | A | 6/1995 | Hagan et al. |
| 5,433,717 | A | 7/1995 | Rubinsky et al. |
| D362,091 | S | 9/1995 | Tomasiak et al. |
| 5,456,703 | A | 10/1995 | Beeuwkes et al. |
| 5,472,416 | A | 12/1995 | Blugerman et al. |
| 5,486,207 | A | 1/1996 | Mahawili |
| 5,497,596 | A | 3/1996 | Zatkulak |
| 5,501,655 | A | 3/1996 | Rolt et al. |
| 5,505,726 | A * | 4/1996 | Meserol ............. A61F 13/0226 606/9 |
| 5,505,730 | A | 4/1996 | Edwards et al. |
| 5,507,790 | A | 4/1996 | Weiss |
| 5,513,629 | A * | 5/1996 | Johnson ............... A61F 7/02 126/263.01 |
| 5,514,105 | A | 5/1996 | Goodman, Jr. et al. |

(56) References Cited

U.S. PATENT DOCUMENTS

| | | |
|---|---|---|
| 5,514,170 A | 5/1996 | Mauch |
| 5,516,505 A | 5/1996 | McDow |
| 5,531,742 A | 7/1996 | Barken |
| 5,558,376 A | 9/1996 | Woehl |
| 5,562,604 A | 10/1996 | Yablon et al. |
| 5,571,801 A | 11/1996 | Segall et al. |
| 5,575,812 A | 11/1996 | Owens et al. |
| 5,603,221 A | 2/1997 | Maytal |
| 5,628,769 A | 5/1997 | Saringer |
| 5,634,890 A | 6/1997 | Morris |
| 5,634,940 A | 6/1997 | Panyard |
| 5,647,051 A | 7/1997 | Neer |
| 5,647,868 A | 7/1997 | Chinn |
| 5,650,450 A | 7/1997 | Lovette et al. |
| 5,651,773 A | 7/1997 | Perry et al. |
| 5,654,279 A | 8/1997 | Rubinsky et al. |
| 5,654,546 A | 8/1997 | Lindsay et al. |
| 5,660,836 A | 8/1997 | Knowlton et al. |
| 5,665,053 A | 9/1997 | Jacobs |
| 5,672,172 A | 9/1997 | Zupkas |
| 5,700,284 A | 12/1997 | Owens et al. |
| 5,725,483 A | 3/1998 | Podolsky |
| 5,733,280 A | 3/1998 | Avitall |
| 5,741,248 A | 4/1998 | Stern et al. |
| 5,746,702 A | 5/1998 | Gelfgat et al. |
| 5,746,736 A | 5/1998 | Tankovich |
| 5,755,663 A | 5/1998 | Larsen et al. |
| 5,755,753 A | 5/1998 | Knowlton et al. |
| 5,755,755 A | 5/1998 | Panyard |
| 5,759,182 A | 6/1998 | Varney et al. |
| 5,759,764 A | 6/1998 | Polovina et al. |
| 5,764,794 A | 6/1998 | Perlin |
| 5,769,879 A | 6/1998 | Richards et al. |
| 5,785,955 A | 7/1998 | Fischer |
| 5,792,080 A | 8/1998 | Ookawa et al. |
| 5,800,490 A | 9/1998 | Patz et al. |
| 5,802,865 A | 9/1998 | Strauss |
| 5,814,040 A | 9/1998 | Nelson et al. |
| D399,493 S | 10/1998 | Nakajima et al. |
| 5,817,050 A | 10/1998 | Klein et al. |
| 5,817,145 A | 10/1998 | Augustine et al. |
| 5,817,149 A | 10/1998 | Owens et al. |
| 5,817,150 A | 10/1998 | Owens et al. |
| 5,830,208 A | 11/1998 | Muller et al. |
| 5,833,685 A | 11/1998 | Tortal et al. |
| 5,844,013 A | 12/1998 | Kenndoff et al. |
| 5,853,364 A | 12/1998 | Baker et al. |
| 5,865,841 A | 2/1999 | Kolen et al. |
| 5,871,524 A | 2/1999 | Knowlton |
| 5,871,526 A | 2/1999 | Gibbs et al. |
| 5,885,211 A | 3/1999 | Eppstein et al. |
| 5,891,617 A | 4/1999 | Watson et al. |
| 5,895,418 A | 4/1999 | Saringer |
| 5,901,707 A | 5/1999 | Goncalves |
| 5,902,256 A | 5/1999 | Benaron |
| 5,919,219 A | 7/1999 | Knowlton et al. |
| 5,944,748 A | 8/1999 | Mager et al. |
| 5,948,011 A | 9/1999 | Knowlton et al. |
| 5,952,168 A | 9/1999 | Wowk et al. |
| 5,954,680 A | 9/1999 | Augustine et al. |
| 5,962,477 A | 10/1999 | Mak |
| 5,964,092 A | 10/1999 | Tozuka et al. |
| 5,964,749 A | 10/1999 | Eckhouse et al. |
| 5,967,976 A | 10/1999 | Larsen et al. |
| 5,980,561 A | 11/1999 | Kolen et al. |
| 5,986,167 A | 11/1999 | Arteman et al. |
| 5,989,286 A | 11/1999 | Owens et al. |
| 5,992,158 A | 11/1999 | Goddard et al. |
| 5,997,530 A | 12/1999 | Nelson et al. |
| 6,017,337 A * | 1/2000 | Pira ........................ A61B 18/02 606/23 |
| 6,023,932 A | 2/2000 | Johnston |
| 6,031,525 A | 2/2000 | Perlin |
| 6,032,675 A | 3/2000 | Rubinsky |
| 6,039,694 A | 3/2000 | Larson et al. |
| 6,041,787 A | 3/2000 | Rubinsky |
| 6,047,215 A | 4/2000 | McClure et al. |
| 6,049,927 A | 4/2000 | Thomas et al. |
| 6,051,159 A | 4/2000 | Hao et al. |
| D424,699 S | 5/2000 | Allen |
| 6,071,239 A | 6/2000 | Cribbs et al. |
| 6,074,415 A | 6/2000 | Der Ovanesian |
| 6,093,230 A | 7/2000 | Johnson et al. |
| 6,102,885 A | 8/2000 | Bass |
| 6,104,952 A | 8/2000 | Tu et al. |
| 6,104,959 A | 8/2000 | Spertell et al. |
| 6,106,517 A | 8/2000 | Zupkas |
| 6,113,558 A | 9/2000 | Rosenschein et al. |
| 6,113,559 A | 9/2000 | Klopotek |
| 6,113,626 A | 9/2000 | Clifton et al. |
| 6,120,519 A | 9/2000 | Weber et al. |
| 6,139,544 A | 10/2000 | Mikus et al. |
| 6,139,545 A | 10/2000 | Utley et al. |
| 6,150,148 A | 11/2000 | Nanda et al. |
| 6,151,735 A | 11/2000 | Koby et al. |
| 6,152,952 A | 11/2000 | Owens et al. |
| 6,171,301 B1 | 1/2001 | Nelson et al. |
| 6,176,869 B1 | 1/2001 | Mason et al. |
| 6,180,867 B1 | 1/2001 | Hedengren et al. |
| 6,224,617 B1 | 5/2001 | Saadat et al. |
| 6,226,996 B1 | 5/2001 | Weber et al. |
| 6,241,753 B1 | 6/2001 | Knowlton |
| 6,264,649 B1 | 7/2001 | Whitcroft et al. |
| 6,273,884 B1 | 8/2001 | Altshuler et al. |
| 6,290,988 B1 | 9/2001 | Van Vilsteren et al. |
| 6,311,090 B1 | 10/2001 | Knowlton |
| 6,311,497 B1 | 11/2001 | Chung |
| 6,312,453 B1 | 11/2001 | Stefanile et al. |
| 6,319,510 B1 | 11/2001 | Yates |
| 6,350,276 B1 | 2/2002 | Knowlton |
| 6,354,297 B1 | 3/2002 | Eiseman |
| 6,357,907 B1 | 3/2002 | Cleveland et al. |
| 6,375,673 B1 | 4/2002 | Clifton et al. |
| 6,377,854 B1 | 4/2002 | Knowlton |
| 6,377,855 B1 | 4/2002 | Knowlton |
| 6,381,497 B1 | 4/2002 | Knowlton |
| 6,381,498 B1 | 4/2002 | Knowlton |
| 6,387,380 B1 | 5/2002 | Knowlton |
| 6,395,467 B1 | 5/2002 | Fahy et al. |
| 6,401,722 B1 | 6/2002 | Krag |
| 6,405,090 B1 | 6/2002 | Knowlton |
| 6,413,255 B1 | 7/2002 | Stern |
| 6,425,912 B1 | 7/2002 | Knowlton |
| 6,426,445 B1 | 7/2002 | Young et al. |
| 6,430,446 B1 | 8/2002 | Knowlton |
| 6,430,956 B1 | 8/2002 | Haas et al. |
| 6,438,424 B1 | 8/2002 | Knowlton |
| 6,438,954 B1 | 8/2002 | Goetz et al. |
| 6,438,964 B1 | 8/2002 | Giblin |
| 6,453,202 B1 | 9/2002 | Knowlton |
| 6,458,888 B1 | 10/2002 | Hood et al. |
| 6,461,378 B1 | 10/2002 | Knowlton |
| 6,470,216 B1 | 10/2002 | Knowlton |
| 6,471,693 B1 | 10/2002 | Carroll et al. |
| 6,475,211 B2 | 11/2002 | Chess et al. |
| 6,478,811 B1 | 11/2002 | Dobak, III et al. |
| 6,494,844 B1 | 12/2002 | Van Bladel et al. |
| 6,497,721 B2 | 12/2002 | Ginsburg et al. |
| 6,508,831 B1 | 1/2003 | Kushnir |
| 6,514,244 B2 | 2/2003 | Pope et al. |
| 6,519,964 B2 | 2/2003 | Bieberich |
| 6,523,354 B1 | 2/2003 | Tolbert |
| D471,982 S | 3/2003 | Cheng |
| 6,527,765 B2 | 3/2003 | Kelman et al. |
| 6,527,798 B2 | 3/2003 | Ginsburg et al. |
| 6,544,248 B1 | 4/2003 | Bass |
| 6,547,811 B1 | 4/2003 | Becker et al. |
| 6,548,297 B1 | 4/2003 | Kuri-Harcuch et al. |
| 6,551,255 B2 | 4/2003 | Van Bladel et al. |
| 6,551,341 B2 | 4/2003 | Boylan et al. |
| 6,551,348 B1 | 4/2003 | Blalock et al. |
| 6,551,349 B2 | 4/2003 | Lasheras et al. |
| 6,569,189 B1 | 5/2003 | Augustine et al. |
| 6,585,652 B2 | 7/2003 | Lang et al. |

(56) References Cited

U.S. PATENT DOCUMENTS

| | | |
|---|---|---|
| 6,592,577 B2 | 7/2003 | Abboud et al. |
| 6,605,080 B1 | 8/2003 | Altshuler et al. |
| 6,607,498 B2 | 8/2003 | Eshel |
| 6,620,187 B2 | 9/2003 | Carson et al. |
| 6,620,188 B1 | 9/2003 | Ginsburg et al. |
| 6,620,189 B1 | 9/2003 | Machold et al. |
| 6,623,430 B1 | 9/2003 | Slayton et al. |
| 6,626,854 B2 | 9/2003 | Friedman et al. |
| 6,632,219 B1 | 10/2003 | Baranov et al. |
| 6,635,053 B1 | 10/2003 | Lalonde et al. |
| 6,643,535 B2 | 11/2003 | Damasco et al. |
| 6,645,162 B2 | 11/2003 | Friedman et al. |
| 6,645,229 B2 | 11/2003 | Matsumura et al. |
| 6,645,232 B2 | 11/2003 | Carson |
| 6,648,904 B2 | 11/2003 | Altshuler et al. |
| 6,656,208 B2 | 12/2003 | Grahn et al. |
| 6,660,027 B2 | 12/2003 | Gruszecki et al. |
| 6,662,054 B2 | 12/2003 | Kreindel et al. |
| 6,682,524 B1 | 1/2004 | Elbrecht et al. |
| 6,682,550 B2 | 1/2004 | Clifton et al. |
| 6,685,731 B2 | 2/2004 | Kushnir et al. |
| 6,694,170 B1 | 2/2004 | Mikus et al. |
| 6,695,874 B2 | 2/2004 | Machold et al. |
| 6,697,670 B2 | 2/2004 | Chornenky |
| 6,699,237 B2 | 3/2004 | Weber et al. |
| 6,699,266 B2 | 3/2004 | Lachenbruch et al. |
| 6,699,267 B2 | 3/2004 | Voorhees et al. |
| 6,718,785 B2 | 4/2004 | Bieberich |
| 6,741,895 B1 | 5/2004 | Gafni et al. |
| 6,743,222 B2 | 6/2004 | Durkin et al. |
| 6,746,474 B2 | 6/2004 | Saadat |
| 6,749,624 B2 | 6/2004 | Knowlton |
| 6,753,182 B1 | 6/2004 | Kadkade et al. |
| 6,764,493 B1 | 7/2004 | Weber et al. |
| 6,764,502 B2 | 7/2004 | Bieberich |
| 6,789,545 B2 | 9/2004 | Littrup et al. |
| 6,795,728 B2 | 9/2004 | Chornenky et al. |
| 6,820,961 B2 | 11/2004 | Johnson |
| 6,821,274 B2 | 11/2004 | McHale et al. |
| 6,840,955 B2 | 1/2005 | Ein |
| 6,849,075 B2 | 2/2005 | Bertolero et al. |
| 6,878,144 B2 | 4/2005 | Altshuler et al. |
| 6,889,090 B2 | 5/2005 | Kreindel |
| 6,892,099 B2 | 5/2005 | Jaafar et al. |
| 6,904,956 B2 | 6/2005 | Noel |
| 6,918,903 B2 | 7/2005 | Bass |
| 6,927,316 B1 | 8/2005 | Faries, Jr. et al. |
| 6,942,022 B2 | 9/2005 | Blangetti et al. |
| 6,945,942 B2 | 9/2005 | Van Bladel et al. |
| 6,948,903 B2 | 9/2005 | Ablabutyan et al. |
| 6,969,399 B2 | 11/2005 | Schock et al. |
| 7,005,558 B1 | 2/2006 | Johansson et al. |
| 7,006,874 B2 | 2/2006 | Knowlton et al. |
| 7,022,121 B2 | 4/2006 | Stern et al. |
| 7,037,326 B2 | 5/2006 | Lee |
| 7,054,685 B2 | 5/2006 | Dimmer et al. |
| 7,060,061 B2 | 6/2006 | Altshuler et al. |
| D525,592 S | 7/2006 | Nguyen |
| 7,077,858 B2 | 7/2006 | Fletcher et al. |
| 7,081,111 B2 | 7/2006 | Svaasand et al. |
| 7,083,612 B2 | 8/2006 | Littrup et al. |
| 7,096,204 B1 | 8/2006 | Chen et al. |
| 7,112,712 B1 | 9/2006 | Ancell |
| 7,115,123 B2 | 10/2006 | Knowlton et al. |
| 7,141,049 B2 | 11/2006 | Stern et al. |
| 7,183,360 B2 | 2/2007 | Daniel et al. |
| 7,189,252 B2 | 3/2007 | Krueger |
| 7,192,426 B2 | 3/2007 | Baust et al. |
| 7,204,832 B2 | 4/2007 | Altshuler et al. |
| 7,220,778 B2 | 5/2007 | Anderson et al. |
| 7,229,436 B2 | 6/2007 | Stern et al. |
| D546,949 S | 7/2007 | Green |
| 7,258,674 B2 | 8/2007 | Cribbs et al. |
| D550,362 S | 9/2007 | Olivera et al. |
| 7,267,675 B2 | 9/2007 | Stern et al. |
| 7,276,058 B2 | 10/2007 | Altshuler et al. |
| 7,318,821 B2 | 1/2008 | Lalonde et al. |
| 7,331,951 B2 | 2/2008 | Eshel et al. |
| 7,347,855 B2 | 3/2008 | Eshel et al. |
| D568,258 S | 5/2008 | Adam |
| 7,367,341 B2 | 5/2008 | Anderson et al. |
| 7,532,201 B2 | 5/2009 | Quistgaard et al. |
| 7,572,268 B2 | 8/2009 | Babaev |
| 7,604,632 B2 | 10/2009 | Howlett et al. |
| 7,613,523 B2 | 11/2009 | Eggers et al. |
| 7,615,016 B2 | 11/2009 | Barthe et al. |
| 7,713,266 B2 | 5/2010 | Elkins et al. |
| 7,780,656 B2 | 8/2010 | Tankovich |
| 7,799,018 B2 | 9/2010 | Goulko |
| 7,824,437 B1 | 11/2010 | Saunders |
| 7,828,831 B1 | 11/2010 | Tanhehco et al. |
| 7,850,683 B2 | 12/2010 | Elkins et al. |
| 7,854,754 B2 | 12/2010 | Ting et al. |
| 7,862,558 B2 | 1/2011 | Elkins et al. |
| RE42,277 E | 4/2011 | Jaafar et al. |
| 7,938,824 B2 | 5/2011 | Chornenky et al. |
| 7,959,657 B1 | 6/2011 | Harsy et al. |
| 7,963,959 B2 | 6/2011 | Da Silva et al. |
| 7,967,763 B2 | 6/2011 | Deem et al. |
| 7,993,330 B2 | 8/2011 | Goulko |
| 7,998,137 B2 | 8/2011 | Elkins et al. |
| RE42,835 E | 10/2011 | Chornenky et al. |
| RE43,009 E | 12/2011 | Chornenky et al. |
| 8,133,180 B2 | 3/2012 | Slayton et al. |
| 8,133,191 B2 | 3/2012 | Rosenberg et al. |
| 8,192,474 B2 | 6/2012 | Levinson |
| 8,246,611 B2 | 8/2012 | Paithankar et al. |
| 8,247,221 B2 | 8/2012 | Fawcett |
| 8,275,442 B2 | 9/2012 | Allison |
| 8,285,390 B2 | 10/2012 | Levinson et al. |
| 8,333,700 B1 | 12/2012 | Barthe et al. |
| 8,337,539 B2 | 12/2012 | Ting et al. |
| 8,366,622 B2 | 2/2013 | Slayton et al. |
| 8,372,130 B2 | 2/2013 | Young et al. |
| 8,397,518 B1 | 3/2013 | Vistakula et al. |
| 8,414,631 B2 | 4/2013 | Quisenberry et al. |
| 8,433,400 B2 | 4/2013 | Prushinskaya et al. |
| 8,506,486 B2 | 8/2013 | Slayton et al. |
| 8,523,775 B2 | 9/2013 | Barthe et al. |
| 8,523,791 B2 | 9/2013 | Castel |
| 8,523,927 B2 | 9/2013 | Levinson et al. |
| 8,535,228 B2 | 9/2013 | Slayton et al. |
| 8,603,073 B2 | 12/2013 | Allison |
| 8,636,665 B2 | 1/2014 | Slayton et al. |
| 8,641,622 B2 | 2/2014 | Barthe et al. |
| 8,663,112 B2 | 3/2014 | Slayton et al. |
| 8,672,848 B2 | 3/2014 | Slayton et al. |
| 8,676,332 B2 | 3/2014 | Fahey |
| 8,690,778 B2 | 4/2014 | Slayton et al. |
| 8,690,779 B2 | 4/2014 | Slayton et al. |
| 8,690,780 B2 | 4/2014 | Slayton et al. |
| 8,702,774 B2 | 4/2014 | Baker et al. |
| 8,758,215 B2 | 6/2014 | Legendre et al. |
| 8,764,693 B1 | 7/2014 | Graham et al. |
| 8,834,547 B2 | 9/2014 | Anderson et al. |
| 9,132,031 B2 | 9/2015 | Levinson et al. |
| 9,149,322 B2 | 10/2015 | Knowlton |
| 9,375,345 B2 | 6/2016 | Levinson et al. |
| 9,581,942 B1 | 2/2017 | Shippert |
| 2001/0005791 A1 | 6/2001 | Ginsburg et al. |
| 2001/0007952 A1 | 7/2001 | Shimizu |
| 2001/0023364 A1 | 9/2001 | Ahn |
| 2001/0031459 A1 | 10/2001 | Fahy et al. |
| 2001/0039439 A1 | 11/2001 | Elkins et al. |
| 2001/0045104 A1 | 11/2001 | Bailey, Sr. et al. |
| 2001/0047196 A1 | 11/2001 | Ginsburg et al. |
| 2002/0026226 A1 | 2/2002 | Ein |
| 2002/0032473 A1 | 3/2002 | Kushnir et al. |
| 2002/0042607 A1 | 4/2002 | Palmer et al. |
| 2002/0049483 A1 | 4/2002 | Knowlton |
| 2002/0058975 A1 | 5/2002 | Bieberich |
| 2002/0062142 A1* | 5/2002 | Knowlton ............ A61N 5/04 607/99 |
| 2002/0068338 A1 | 6/2002 | Nanda et al. |

(56) References Cited

U.S. PATENT DOCUMENTS

| | | |
|---|---|---|
| 2002/0068874 A1 | 6/2002 | Zuckerwar et al. |
| 2002/0082668 A1 | 6/2002 | Ingman |
| 2002/0103520 A1 | 8/2002 | Latham |
| 2002/0107558 A1 | 8/2002 | Clifton et al. |
| 2002/0117293 A1 | 8/2002 | Campbell |
| 2002/0120315 A1 | 8/2002 | Furuno et al. |
| 2002/0128648 A1 | 9/2002 | Weber et al. |
| 2002/0151830 A1 | 10/2002 | Kahn |
| 2002/0151887 A1 | 10/2002 | Stern et al. |
| 2002/0156509 A1 | 10/2002 | Cheung |
| 2002/0161357 A1 | 10/2002 | Anderson et al. |
| 2002/0188286 A1 | 12/2002 | Quijano et al. |
| 2002/0198518 A1 | 12/2002 | Mikus et al. |
| 2003/0032900 A1 | 2/2003 | Ella |
| 2003/0044764 A1 | 3/2003 | Soane et al. |
| 2003/0055414 A1 | 3/2003 | Altshuler et al. |
| 2003/0062040 A1 | 4/2003 | Lurie et al. |
| 2003/0069618 A1 | 4/2003 | Smith, III et al. |
| 2003/0077326 A1 | 4/2003 | Newton et al. |
| 2003/0077329 A1* | 4/2003 | Kipp ................ A61K 8/02 424/489 |
| 2003/0079488 A1 | 5/2003 | Bieberich |
| 2003/0100936 A1 | 5/2003 | Altshuler et al. |
| 2003/0109908 A1 | 6/2003 | Lachenbruch et al. |
| 2003/0109910 A1 | 6/2003 | Lachenbruch et al. |
| 2003/0109911 A1 | 6/2003 | Lachenbruch et al. |
| 2003/0109912 A1 | 6/2003 | Joye et al. |
| 2003/0114885 A1 | 6/2003 | Nova et al. |
| 2003/0120268 A1 | 6/2003 | Bertolero et al. |
| 2003/0125649 A1 | 7/2003 | McIntosh et al. |
| 2003/0187488 A1 | 10/2003 | Kreindel et al. |
| 2003/0199226 A1 | 10/2003 | Sommer et al. |
| 2003/0199859 A1 | 10/2003 | Altshuler et al. |
| 2003/0220594 A1 | 11/2003 | Halvorson et al. |
| 2003/0220635 A1 | 11/2003 | Knowlton et al. |
| 2003/0220674 A1 | 11/2003 | Anderson et al. |
| 2003/0236487 A1 | 12/2003 | Knowlton |
| 2004/0002705 A1 | 1/2004 | Knowlton et al. |
| 2004/0006328 A1 | 1/2004 | Anderson |
| 2004/0009936 A1* | 1/2004 | Tang ................ A61K 38/193 514/44 R |
| 2004/0024437 A1 | 2/2004 | Machold et al. |
| 2004/0030332 A1 | 2/2004 | Knowlton et al. |
| 2004/0034341 A1 | 2/2004 | Altshuler et al. |
| 2004/0039312 A1 | 2/2004 | Hillstead et al. |
| 2004/0044384 A1 | 3/2004 | Leber et al. |
| 2004/0049178 A1 | 3/2004 | Abboud et al. |
| 2004/0073079 A1 | 4/2004 | Altshuler et al. |
| 2004/0074629 A1 | 4/2004 | Noel |
| 2004/0077977 A1 | 4/2004 | Ella et al. |
| 2004/0082886 A1 | 4/2004 | Timpson |
| 2004/0093042 A1 | 5/2004 | Altshuler et al. |
| 2004/0102768 A1 | 5/2004 | Cluzeau et al. |
| 2004/0104012 A1 | 6/2004 | Zhou et al. |
| 2004/0106867 A1 | 6/2004 | Eshel et al. |
| 2004/0133251 A1 | 7/2004 | Altshuler et al. |
| 2004/0159109 A1 | 8/2004 | Harvie |
| 2004/0162596 A1 | 8/2004 | Altshuler et al. |
| 2004/0176667 A1 | 9/2004 | Mihai et al. |
| 2004/0186535 A1 | 9/2004 | Knowlton |
| 2004/0199226 A1 | 10/2004 | Shadduck |
| 2004/0206365 A1 | 10/2004 | Knowlton |
| 2004/0210214 A1 | 10/2004 | Knowlton |
| 2004/0210287 A1 | 10/2004 | Greene |
| 2004/0215294 A1 | 10/2004 | Littrup et al. |
| 2004/0249427 A1 | 12/2004 | Nabilsi et al. |
| 2004/0259855 A1 | 12/2004 | Anderson et al. |
| 2004/0260209 A1 | 12/2004 | Ella et al. |
| 2004/0260210 A1 | 12/2004 | Ella et al. |
| 2004/0260211 A1 | 12/2004 | Maalouf |
| 2004/0267339 A1 | 12/2004 | Yon et al. |
| 2005/0010197 A1 | 1/2005 | Lau et al. |
| 2005/0033957 A1 | 2/2005 | Enokida |
| 2005/0038422 A1 | 2/2005 | Maurice |
| 2005/0049526 A1 | 3/2005 | Baer |
| 2005/0049543 A1 | 3/2005 | Anderson et al. |
| 2005/0049661 A1 | 3/2005 | Koffroth |
| 2005/0065531 A1 | 3/2005 | Cohen |
| 2005/0113725 A1 | 5/2005 | Masuda |
| 2005/0143781 A1 | 6/2005 | Carbunaru et al. |
| 2005/0145372 A1 | 7/2005 | Noel |
| 2005/0149153 A1 | 7/2005 | Nakase et al. |
| 2005/0154314 A1 | 7/2005 | Quistgaard |
| 2005/0154431 A1 | 7/2005 | Quistgaard et al. |
| 2005/0159986 A1 | 7/2005 | Breeland et al. |
| 2005/0177075 A1 | 8/2005 | Meunier et al. |
| 2005/0182462 A1 | 8/2005 | Chornenky et al. |
| 2005/0187495 A1 | 8/2005 | Quistgaard et al. |
| 2005/0187502 A1 | 8/2005 | Krempel et al. |
| 2005/0187597 A1 | 8/2005 | Vanderschuit |
| 2005/0203446 A1 | 9/2005 | Takashima |
| 2005/0215987 A1 | 9/2005 | Slatkine |
| 2005/0222565 A1 | 10/2005 | Manstein |
| 2005/0251117 A1 | 11/2005 | Anderson et al. |
| 2005/0251120 A1* | 11/2005 | Anderson ............ A61B 5/6804 606/20 |
| 2005/0261753 A1 | 11/2005 | Littrup et al. |
| 2005/0277859 A1 | 12/2005 | Carlsmith et al. |
| 2005/0281789 A1 | 12/2005 | Rao et al. |
| 2005/0283144 A1 | 12/2005 | Shiono et al. |
| 2006/0030778 A1 | 2/2006 | Mendlein et al. |
| 2006/0035380 A1 | 2/2006 | Saint-Leger |
| 2006/0036300 A1 | 2/2006 | Kreindel |
| 2006/0041704 A1 | 2/2006 | Choi |
| 2006/0074313 A1 | 4/2006 | Slayton et al. |
| 2006/0079852 A1 | 4/2006 | Bubb et al. |
| 2006/0094988 A1 | 5/2006 | Tosaya et al. |
| 2006/0106836 A1 | 5/2006 | Masugi et al. |
| 2006/0111613 A1 | 5/2006 | Boutillette et al. |
| 2006/0122509 A1 | 6/2006 | Desilets |
| 2006/0188832 A1 | 8/2006 | McCarren |
| 2006/0189964 A1 | 8/2006 | Anderson et al. |
| 2006/0195168 A1 | 8/2006 | Dunbar et al. |
| 2006/0200063 A1 | 9/2006 | Munro et al. |
| 2006/0206040 A1 | 9/2006 | Greenberg et al. |
| 2006/0206110 A1 | 9/2006 | Knowlton et al. |
| 2006/0234899 A1 | 10/2006 | Nekmard et al. |
| 2006/0259102 A1 | 11/2006 | Slatkine |
| 2006/0265032 A1 | 11/2006 | Hennings et al. |
| 2006/0270745 A1 | 11/2006 | Hunt et al. |
| 2006/0293734 A1 | 12/2006 | Scott et al. |
| 2007/0010811 A1 | 1/2007 | Stern et al. |
| 2007/0010861 A1 | 1/2007 | Anderson et al. |
| 2007/0032561 A1 | 2/2007 | Lin et al. |
| 2007/0038156 A1 | 2/2007 | Rosenberg |
| 2007/0055156 A1 | 3/2007 | Desilets et al. |
| 2007/0055173 A1 | 3/2007 | DeLonzor et al. |
| 2007/0055179 A1 | 3/2007 | Deem et al. |
| 2007/0055180 A1 | 3/2007 | Deem et al. |
| 2007/0055181 A1 | 3/2007 | Deem et al. |
| 2007/0073367 A1 | 3/2007 | Jones et al. |
| 2007/0078502 A1 | 4/2007 | Weber et al. |
| 2007/0088413 A1 | 4/2007 | Weber et al. |
| 2007/0100398 A1 | 5/2007 | Sloan |
| 2007/0106342 A1 | 5/2007 | Schumann |
| 2007/0123962 A1 | 5/2007 | Grahn et al. |
| 2007/0129441 A1 | 6/2007 | Koulen |
| 2007/0129714 A1* | 6/2007 | Elkins ................ A61B 18/02 606/21 |
| 2007/0135876 A1 | 6/2007 | Weber |
| 2007/0141265 A1 | 6/2007 | Thomson |
| 2007/0179482 A1 | 8/2007 | Anderson |
| 2007/0193278 A1 | 8/2007 | Polacek et al. |
| 2007/0198071 A1 | 8/2007 | Ting et al. |
| 2007/0219540 A1 | 9/2007 | Masotti et al. |
| 2007/0233226 A1 | 10/2007 | Kochamba et al. |
| 2007/0239062 A1 | 10/2007 | Chopra et al. |
| 2007/0239075 A1 | 10/2007 | Rosenberg et al. |
| 2007/0239150 A1 | 10/2007 | Zvuloni et al. |
| 2007/0249519 A1 | 10/2007 | Guha et al. |
| 2007/0255187 A1 | 11/2007 | Branch |
| 2007/0255274 A1 | 11/2007 | Stern et al. |
| 2007/0255362 A1 | 11/2007 | Levinson et al. |
| 2007/0265585 A1 | 11/2007 | Joshi et al. |

(56) References Cited

U.S. PATENT DOCUMENTS

| | | |
|---|---|---|
| 2007/0265614 A1 | 11/2007 | Stern et al. |
| 2007/0270925 A1 | 11/2007 | Levinson |
| 2007/0282249 A1 | 12/2007 | Quisenberry et al. |
| 2007/0282318 A1 | 12/2007 | Spooner et al. |
| 2008/0014627 A1 | 1/2008 | Merchant et al. |
| 2008/0046047 A1 | 2/2008 | Jacobs |
| 2008/0058784 A1 | 3/2008 | Manstein et al. |
| 2008/0077201 A1 | 3/2008 | Levinson et al. |
| 2008/0077202 A1 | 3/2008 | Levinson |
| 2008/0077211 A1 | 3/2008 | Levinson et al. |
| 2008/0097207 A1 | 4/2008 | Cai et al. |
| 2008/0139901 A1 | 6/2008 | Altshuler et al. |
| 2008/0140061 A1 | 6/2008 | Toubia et al. |
| 2008/0140371 A1 | 6/2008 | Warner |
| 2008/0160480 A1 | 7/2008 | Ruddle et al. |
| 2008/0161892 A1 | 7/2008 | Mercuro et al. |
| 2008/0183164 A1 | 7/2008 | Elkins et al. |
| 2008/0188915 A1 | 8/2008 | Mills et al. |
| 2008/0195036 A1 | 8/2008 | Merchant et al. |
| 2008/0248554 A1 | 10/2008 | Merchant et al. |
| 2008/0269851 A1 | 10/2008 | Deem et al. |
| 2008/0287839 A1 | 11/2008 | Rosen et al. |
| 2008/0300529 A1 | 12/2008 | Reinstein |
| 2008/0312651 A1 | 12/2008 | Pope et al. |
| 2009/0012434 A1 | 1/2009 | Anderson |
| 2009/0016980 A1 | 1/2009 | Tsivkin et al. |
| 2009/0018623 A1 | 1/2009 | Levinson et al. |
| 2009/0018624 A1 | 1/2009 | Levinson et al. |
| 2009/0018625 A1 | 1/2009 | Levinson et al. |
| 2009/0018626 A1 | 1/2009 | Levinson et al. |
| 2009/0018627 A1 | 1/2009 | Levinson et al. |
| 2009/0024023 A1 | 1/2009 | Welches et al. |
| 2009/0076488 A1 | 3/2009 | Welches et al. |
| 2009/0112134 A1 | 4/2009 | Avni |
| 2009/0118722 A1 | 5/2009 | Ebbers et al. |
| 2009/0149929 A1 | 6/2009 | Levinson et al. |
| 2009/0149930 A1 | 6/2009 | Schenck |
| 2009/0171253 A1 | 7/2009 | Davenport |
| 2009/0171334 A1 | 7/2009 | Elkins et al. |
| 2009/0209886 A1 | 8/2009 | Tudico |
| 2009/0221938 A1 | 9/2009 | Rosenberg et al. |
| 2009/0226424 A1 | 9/2009 | Hsu |
| 2009/0276018 A1 | 11/2009 | Brader |
| 2009/0281464 A1 | 11/2009 | Cioanta et al. |
| 2009/0299234 A1 | 12/2009 | Cho et al. |
| 2009/0306749 A1 | 12/2009 | Mulindwa |
| 2009/0312676 A1 | 12/2009 | Rousso et al. |
| 2009/0312693 A1 | 12/2009 | Thapliyal et al. |
| 2009/0326621 A1 | 12/2009 | El-Galley |
| 2010/0015190 A1 | 1/2010 | Hassler |
| 2010/0028969 A1 | 2/2010 | Mueller et al. |
| 2010/0030306 A1 | 2/2010 | Edelman et al. |
| 2010/0036295 A1 | 2/2010 | Altshuler et al. |
| 2010/0042087 A1 | 2/2010 | Goldboss et al. |
| 2010/0047360 A1 | 2/2010 | Klaveness et al. |
| 2010/0049178 A1 | 2/2010 | Deem et al. |
| 2010/0081971 A1 | 4/2010 | Allison |
| 2010/0087806 A1 | 4/2010 | Da Silva et al. |
| 2010/0152824 A1 | 6/2010 | Allison |
| 2010/0168726 A1 | 7/2010 | Brookman |
| 2010/0179531 A1 | 7/2010 | Nebrigic et al. |
| 2010/0198064 A1 | 8/2010 | Perl et al. |
| 2010/0198204 A1 | 8/2010 | Rogers |
| 2010/0217349 A1 | 8/2010 | Fahey et al. |
| 2010/0241023 A1 | 9/2010 | Gilbert |
| 2010/0268220 A1 | 10/2010 | Johnson et al. |
| 2010/0280582 A1 | 11/2010 | Baker et al. |
| 2011/0009860 A1 | 1/2011 | Chornenky et al. |
| 2011/0040235 A1 | 2/2011 | Castel |
| 2011/0040299 A1 | 2/2011 | Kim et al. |
| 2011/0046523 A1 | 2/2011 | Altshuler et al. |
| 2011/0060242 A1 | 3/2011 | Hausman et al. |
| 2011/0060323 A1 | 3/2011 | Baust et al. |
| 2011/0066083 A1 | 3/2011 | Tosaya et al. |
| 2011/0066216 A1 | 3/2011 | Ting et al. |
| 2011/0077557 A1 | 3/2011 | Wing et al. |
| 2011/0077723 A1 | 3/2011 | Parish et al. |
| 2011/0112405 A1 | 5/2011 | Barthe et al. |
| 2011/0112520 A1 | 5/2011 | Kreindel |
| 2011/0144631 A1 | 6/2011 | Elkins et al. |
| 2011/0152849 A1 | 6/2011 | Baust et al. |
| 2011/0172651 A1 | 7/2011 | Altshuler et al. |
| 2011/0189129 A1 | 8/2011 | Qiu et al. |
| 2011/0196395 A1 | 8/2011 | Maschke |
| 2011/0196438 A1 | 8/2011 | Mnozil et al. |
| 2011/0202048 A1 | 8/2011 | Nebrigic et al. |
| 2011/0238050 A1 | 9/2011 | Allison et al. |
| 2011/0238051 A1 | 9/2011 | Levinson et al. |
| 2011/0257642 A1 | 10/2011 | Griggs, III |
| 2011/0288537 A1 | 11/2011 | Halaka |
| 2011/0300079 A1 | 12/2011 | Martens et al. |
| 2011/0301585 A1 | 12/2011 | Goulko |
| 2011/0313411 A1 | 12/2011 | Anderson et al. |
| 2011/0313412 A1 | 12/2011 | Kim et al. |
| 2012/0010609 A1 | 1/2012 | Deem et al. |
| 2012/0016239 A1 | 1/2012 | Barthe et al. |
| 2012/0022518 A1 | 1/2012 | Levinson |
| 2012/0022622 A1 | 1/2012 | Johnson et al. |
| 2012/0035475 A1 | 2/2012 | Barthe et al. |
| 2012/0035476 A1 | 2/2012 | Barthe et al. |
| 2012/0041525 A1 | 2/2012 | Karni |
| 2012/0046547 A1 | 2/2012 | Barthe et al. |
| 2012/0053458 A1 | 3/2012 | Barthe et al. |
| 2012/0065629 A1 | 3/2012 | Elkins et al. |
| 2012/0083862 A1 | 4/2012 | Altshuler et al. |
| 2012/0101549 A1 | 4/2012 | Schumann |
| 2012/0109041 A1 | 5/2012 | Munz |
| 2012/0158100 A1 | 6/2012 | Schomacker |
| 2012/0209363 A1 | 8/2012 | Williams, III et al. |
| 2012/0233736 A1 | 9/2012 | Tepper et al. |
| 2012/0239123 A1 | 9/2012 | Weber et al. |
| 2012/0253416 A1 | 10/2012 | Erez et al. |
| 2012/0259322 A1 | 10/2012 | Fourkas et al. |
| 2012/0277674 A1 | 11/2012 | Clark, III et al. |
| 2012/0310232 A1 | 12/2012 | Erez |
| 2013/0018236 A1 | 1/2013 | Altshuler et al. |
| 2013/0019374 A1 | 1/2013 | Schwartz |
| 2013/0035680 A1 | 2/2013 | Ben-haim et al. |
| 2013/0066309 A1 | 3/2013 | Levinson |
| 2013/0073017 A1 | 3/2013 | Liu et al. |
| 2013/0079684 A1 | 3/2013 | Rosen et al. |
| 2013/0116758 A1 | 5/2013 | Levinson et al. |
| 2013/0116759 A1 | 5/2013 | Levinson et al. |
| 2013/0150844 A1 | 6/2013 | Deem et al. |
| 2013/0158440 A1 | 6/2013 | Allison |
| 2013/0158636 A1 | 6/2013 | Ting et al. |
| 2013/0166003 A1 | 6/2013 | Johnson et al. |
| 2013/0190744 A1 | 7/2013 | Avram et al. |
| 2013/0238062 A1 | 9/2013 | Ron Edoute et al. |
| 2013/0245507 A1 | 9/2013 | Khorassani Zadeh |
| 2013/0253384 A1 | 9/2013 | Anderson et al. |
| 2013/0253493 A1 | 9/2013 | Anderson et al. |
| 2013/0253494 A1 | 9/2013 | Anderson et al. |
| 2013/0253495 A1 | 9/2013 | Anderson et al. |
| 2013/0253496 A1 | 9/2013 | Anderson et al. |
| 2013/0303904 A1 | 11/2013 | Barthe et al. |
| 2013/0303905 A1 | 11/2013 | Barthe et al. |
| 2013/0331914 A1 | 12/2013 | Lee et al. |
| 2014/0005759 A1 | 1/2014 | Fahey et al. |
| 2014/0005760 A1 | 1/2014 | Levinson et al. |
| 2014/0067025 A1 | 3/2014 | Levinson et al. |
| 2014/0142469 A1 | 5/2014 | Britva et al. |
| 2014/0200487 A1 | 7/2014 | Ramdas et al. |
| 2014/0200488 A1 | 7/2014 | Seo et al. |
| 2014/0222121 A1 | 8/2014 | Spence et al. |
| 2014/0277219 A1 | 9/2014 | Nanda |
| 2014/0277302 A1 | 9/2014 | Weber et al. |
| 2014/0277303 A1 | 9/2014 | Biser et al. |
| 2014/0303697 A1 | 10/2014 | Anderson et al. |
| 2015/0112412 A1 | 4/2015 | Anderson et al. |
| 2015/0141797 A1 | 5/2015 | Turnquist et al. |
| 2015/0209174 A1 | 7/2015 | Abreu |
| 2015/0216719 A1 | 8/2015 | DeBenedictis et al. |
| 2015/0216720 A1 | 8/2015 | DeBenedictis et al. |

(56) References Cited

U.S. PATENT DOCUMENTS

| | | |
|---|---|---|
| 2015/0216816 A1 | 8/2015 | O'Neil et al. |
| 2015/0223975 A1 | 8/2015 | Anderson et al. |
| 2015/0283022 A1 | 10/2015 | Lee et al. |
| 2015/0328077 A1 | 11/2015 | Levinson |
| 2015/0328478 A1 | 11/2015 | McDaniel |
| 2015/0335468 A1 | 11/2015 | Rose et al. |
| 2015/0342780 A1 | 12/2015 | Levinson et al. |
| 2016/0051308 A1 | 2/2016 | Pennybacker et al. |
| 2016/0051401 A1 | 2/2016 | Yee et al. |
| 2016/0135985 A1 | 5/2016 | Anderson |
| 2016/0220849 A1 | 8/2016 | Knowlton |
| 2016/0324684 A1 | 11/2016 | Levinson et al. |
| 2017/0007309 A1 | 1/2017 | DeBenedictis et al. |
| 2017/0065323 A1 | 3/2017 | Rosen et al. |
| 2017/0079833 A1 | 3/2017 | Frangineas, Jr. et al. |
| 2017/0105869 A1 | 4/2017 | Frangineas, Jr. et al. |
| 2017/0165105 A1 | 6/2017 | Anderson et al. |
| 2017/0196731 A1 | 7/2017 | DeBenedictis et al. |
| 2017/0239079 A1 | 8/2017 | Root et al. |
| 2017/0319378 A1 | 11/2017 | Anderson et al. |
| 2017/0325992 A1 | 11/2017 | DeBenedictis et al. |
| 2017/0325993 A1 | 11/2017 | Jimenez Lozano et al. |
| 2017/0326042 A1 | 11/2017 | Zeng et al. |
| 2017/0326346 A1 | 11/2017 | Jimenez Lozano et al. |
| 2018/0185081 A1 | 7/2018 | O'neil et al. |
| 2018/0185189 A1 | 7/2018 | Weber et al. |
| 2018/0263677 A1 | 9/2018 | Hilton et al. |
| 2018/0271767 A1 | 9/2018 | Jimenez Lozano et al. |
| 2018/0310950 A1 | 11/2018 | Yee et al. |
| 2019/0000663 A1 | 1/2019 | Anderson et al. |
| 2019/0125424 A1 | 5/2019 | DeBenedictis et al. |
| 2019/0142493 A1 | 5/2019 | Debenedictis et al. |
| 2019/0224042 A1 | 7/2019 | Ting et al. |

FOREIGN PATENT DOCUMENTS

| | | | |
|---|---|---|---|
| CA | 2585214 A1 | 10/2007 | |
| CH | 333982 A | 11/1958 | |
| CN | 86200604 U | 10/1987 | |
| CN | 2514795 Y | 10/2002 | |
| CN | 2514811 Y | 10/2002 | |
| CN | 2617189 Y | 5/2004 | |
| CN | 1511503 A | 7/2004 | |
| CN | 1741777 A | 3/2006 | |
| CN | 1817990 A | 8/2006 | |
| CN | 2843367 Y | 12/2006 | |
| CN | 2850584 Y | 12/2006 | |
| CN | 2850585 Y | 12/2006 | |
| CN | 200970265 Y | 11/2007 | |
| CN | 101259329 A | 9/2008 | |
| CN | 101309657 A | 11/2008 | |
| CN | 101351167 A | 1/2009 | |
| CN | 101489541 A | 7/2009 | |
| DE | 532976 C | 9/1931 | |
| DE | 2851602 A1 | 6/1980 | |
| DE | 4213584 A1 | 11/1992 | |
| DE | 4224595 A1 | 1/1994 | |
| DE | 4238291 A1 | 5/1994 | |
| DE | 4445627 A1 | 6/1996 | |
| DE | 19800416 A1 | 7/1999 | |
| EP | 263069 A2 | 4/1988 | |
| EP | 0397043 A1 | 11/1990 | |
| EP | 0406244 A1 | 1/1991 | |
| EP | 560309 A1 | 9/1993 | |
| EP | 0598824 A1 | 6/1994 | |
| EP | 1030611 A1 | 8/2000 | |
| EP | 1201266 A1 | 5/2002 | |
| EP | 0573573 B2 * | 7/2003 | ............... A61K 9/70 |
| EP | 1568395 A1 | 8/2005 | |
| EP | 2260801 A2 | 12/2010 | |
| EP | 2289598 A1 | 3/2011 | |
| EP | 2527005 A1 | 11/2012 | |
| EP | 2904986 A1 | 8/2015 | |
| FR | 854937 A | 4/1940 | |
| FR | 2744358 A1 | 8/1997 | |
| FR | 2745935 A1 | 9/1997 |
| FR | 2767476 A1 | 2/1999 |
| FR | 2776920 A1 | 10/1999 |
| FR | 2789893 A1 | 8/2000 |
| FR | 2805989 A1 | 9/2001 |
| GB | 387960 A | 2/1933 |
| GB | 578157 A | 6/1946 |
| GB | 2120944 A | 12/1983 |
| GB | 2202447 A | 9/1988 |
| GB | 2248183 A | 4/1992 |
| GB | 2263872 A | 8/1993 |
| GB | 2286660 A | 8/1995 |
| GB | 2323659 A | 9/1998 |
| JP | S50-33039 Y2 | 9/1975 |
| JP | 58187454 A | 11/1983 |
| JP | S6094113 U | 6/1985 |
| JP | 62082977 A | 4/1987 |
| JP | 63076895 A | 4/1988 |
| JP | 01223961 A | 9/1989 |
| JP | 03051964 A | 3/1991 |
| JP | 03259975 A | 11/1991 |
| JP | 04093597 A | 3/1992 |
| JP | 06261933 A | 9/1994 |
| JP | 07194666 A | 8/1995 |
| JP | 07268274 A | 10/1995 |
| JP | 09164163 A | 6/1997 |
| JP | 10216169 A | 8/1998 |
| JP | 10223961 A | 8/1998 |
| JP | 3065657 U | 2/2000 |
| JP | 2000503154 A | 3/2000 |
| JP | 3065657 B2 | 7/2000 |
| JP | 2001046416 A | 2/2001 |
| JP | 2002125993 A | 5/2002 |
| JP | 2002224051 A | 8/2002 |
| JP | 2002282295 A | 10/2002 |
| JP | 2002290397 A | 10/2002 |
| JP | 2002543668 A | 12/2002 |
| JP | 2003190201 A | 7/2003 |
| JP | 2004013600 A | 1/2004 |
| JP | 2004073812 A | 3/2004 |
| JP | 2004159666 A | 6/2004 |
| JP | 2005039790 A | 2/2005 |
| JP | 2005065984 A | 3/2005 |
| JP | 2005110755 A | 4/2005 |
| JP | 2005509977 A | 4/2005 |
| JP | 3655820 B2 | 6/2005 |
| JP | 2005520608 A | 7/2005 |
| JP | 2005237908 A | 9/2005 |
| JP | 2005323716 A | 11/2005 |
| JP | 2006026001 A | 2/2006 |
| JP | 2006130055 A | 5/2006 |
| JP | 2006520949 A | 9/2006 |
| JP | 2007270459 A | 10/2007 |
| JP | 2008532591 A | 8/2008 |
| JP | 2009515232 A | 4/2009 |
| JP | 2009189757 A | 8/2009 |
| KR | 200173222 Y1 | 12/1999 |
| KR | 10-2004-0094508 A | 11/2004 |
| KR | 20090000258 U | 1/2009 |
| KR | 1020130043299 A | 4/2013 |
| KR | 1020140038165 A | 3/2014 |
| RU | 2036667 C1 | 6/1995 |
| SU | 532976 A1 | 11/1978 |
| TW | 0476644 B | 2/2002 |
| WO | 8503216 A1 | 8/1985 |
| WO | 9114417 A1 | 10/1991 |
| WO | 9300807 A1 | 1/1993 |
| WO | 9404116 A1 | 3/1994 |
| WO | 9623447 A1 | 8/1996 |
| WO | 9626693 A1 | 9/1996 |
| WO | 9636293 A1 | 11/1996 |
| WO | 9637158 A1 | 11/1996 |
| WO | 9704832 A1 | 2/1997 |
| WO | 9705828 A1 | 2/1997 |
| WO | 9722262 A2 | 6/1997 |
| WO | 9724088 A1 | 7/1997 |
| WO | 9725798 A1 | 7/1997 |
| WO | 9748440 A1 | 12/1997 |
| WO | 9829134 A2 | 7/1998 |

(56) References Cited

FOREIGN PATENT DOCUMENTS

| | | |
|---|---|---|
| WO | 9831321 A1 | 7/1998 |
| WO | 9841156 A1 | 9/1998 |
| WO | 9841157 A1 | 9/1998 |
| WO | 9909928 A1 | 3/1999 |
| WO | 9916502 A1 | 4/1999 |
| WO | 9938469 A1 | 8/1999 |
| WO | 9949937 A1 | 10/1999 |
| WO | 0044346 A1 | 8/2000 |
| WO | 0044349 A1 | 8/2000 |
| WO | 0065770 A1 | 11/2000 |
| WO | 0067685 A1 | 11/2000 |
| WO | 0100269 A1 | 1/2001 |
| WO | 0113989 A1 | 3/2001 |
| WO | 0114012 A1 | 3/2001 |
| WO | 0134048 A1 | 5/2001 |
| WO | 0205736 A1 | 1/2002 |
| WO | 02102921 A1 | 12/2002 |
| WO | 03007859 A1 | 1/2003 |
| WO | 03078596 A2 | 9/2003 |
| WO | 03079916 A1 | 10/2003 |
| WO | 2004000098 A2 | 12/2003 |
| WO | 2004080279 A2 | 9/2004 |
| WO | 2004090939 A2 | 10/2004 |
| WO | WO-2005/018433 A2 | 3/2005 |
| WO | WO-2005/023200 A2 | 3/2005 |
| WO | 2005033957 A1 | 4/2005 |
| WO | 2005046540 A1 | 5/2005 |
| WO | 2005060354 A2 | 7/2005 |
| WO | 2005096979 A1 | 10/2005 |
| WO | 2005112815 A1 | 12/2005 |
| WO | 2006066226 A1 | 6/2006 |
| WO | 2006094348 A1 | 9/2006 |
| WO | 2006106836 A1 | 10/2006 |
| WO | 2006116603 A2 | 11/2006 |
| WO | 2006127467 A2 | 11/2006 |
| WO | 2007012083 A2 | 1/2007 |
| WO | 2007028975 A1 | 3/2007 |
| WO | 2007041642 A2 | 4/2007 |
| WO | 2007101039 A1 | 9/2007 |
| WO | 2007127924 A2 | 11/2007 |
| WO | 2007145421 A1 | 12/2007 |
| WO | 2007145422 A1 | 12/2007 |
| WO | 2008006018 A2 | 1/2008 |
| WO | 2008039556 A1 | 4/2008 |
| WO | 2008039557 A1 | 4/2008 |
| WO | 2008055243 A2 | 5/2008 |
| WO | 2008143678 A1 | 11/2008 |
| WO | 2009011708 A1 | 1/2009 |
| WO | 2009026471 A1 | 2/2009 |
| WO | 2010077841 A1 | 7/2010 |
| WO | 2010127315 A2 | 11/2010 |
| WO | 2012012296 A1 | 1/2012 |
| WO | 2012103242 A1 | 8/2012 |
| WO | 2013013059 A1 | 1/2013 |
| WO | 2013075006 A1 | 5/2013 |
| WO | 2013075016 A1 | 5/2013 |
| WO | 2013190337 A1 | 12/2013 |
| WO | 2014151872 A3 | 9/2014 |
| WO | 2014191263 A1 | 12/2014 |
| WO | 2015117001 A1 | 8/2015 |
| WO | 2015117005 A1 | 8/2015 |
| WO | 2015117026 A2 | 8/2015 |
| WO | 2015117032 A1 | 8/2015 |
| WO | 2015117036 A2 | 8/2015 |
| WO | 2016028796 A1 | 2/2016 |
| WO | 2016048721 A1 | 3/2016 |

OTHER PUBLICATIONS

Al-Sakere, B. et al. "Tumor Ablation with Irreversible Electroporation," PLOS One, Issue 11, Nov. 2007, 8 pages.

Alster, T. et al., "Cellulite Treatment Using a Novel Combination Radiofrequency, Infrared Light, and Mechanical Tissue Manipulation Device," Journal of Cosmetic and Laser Therapy, vol. 7, 2005, pp. 81-85.

Ardevol, A. et al., "Cooling Rates of Tissue Samples During Freezing with Liquid Nitrogen," Journal of Biochemical and Biophysical Methods, vol. 27, 1993, pp. 77-86.

Arena, C. B. et al., "High-Frequency Irreversible Electroporation (H-FIRE) for Non-Thermal Ablation Without Muscle Contraction," BioMedical Engineering OnLine 2011, 10:102, Nov. 21, 2011, 21 pgs.

Becker, S. M. et al. "Local Temperature Rises Influence In Vivo Electroporation Pore Development: A Numerical Stratum Corneum Lipid Phase Transition Model," Journal of Biomechanical Engineering, vol. 129, Oct. 2007, pp. 712-721.

Bohm, T. et al., "Saline-Enhanced Radiofrequency Ablation of Breast Tissue: an in Vitro Feasibility Study," Investigative Radiology, vol. 35 (3), 2000, pp. 149-157.

Bondei, E. et al., "Disorders of Subcutaneous Tissue (Cold Panniculitis)," Dermatology in General Medicine, Fourth Edition, vol. 1, Chapter 108, 1993, Section 16, pp. 1333-1334.

Burge, S.M. et al., "Hair Follicle Destruction and Regeneration in Guinea Pig Skin after Cutaneous Freeze Injury," Cryobiology, 27(2), 1990, pp. 153-163.

Coban, Y. K. et al., "Ischemia-Reperfusion Injury of Adipofascial Tissue: An Experimental Study Evaluating Early Histologic and Biochemical Alterations in Rats," Mediators of Inflammation, 2005, 5, pp. 304-308.

Del Pino, M. E. et al. "Effect of Controlled Volumetric Tissue Heating with Radiofrequency on Cellulite and the Subcutaneous Tissue of the Buttocks and Thighs," Journal of Drugs in Dermatology, vol. 5, Issue 8, Sep. 2006, pp. 714-722.

Donski, P. K. et al., "The Effects of Cooling no Experimental Free Flap Survival," British Journal of Plastic Surgery, vol. 33, 1980, pp. 353-360.

Duck, F. A., Physical Properties of Tissue, Academic Press Ltd., chapters 4 & 5, 1990, pp. 73-165.

Duncan, W. C. et al., "Cold Panniculitis," Archives of Dermatology, vol. 94, Issue 6, Dec. 1966, pp. 722-724.

Epstein, E. H. et al., "Popsicle Panniculitis," The New England Journal of Medicine, 282(17), Apr. 23, 1970, pp. 966-967.

Fournier, L. et al. "Lattice Model for the Kinetics of Rupture of Fluid Bilayer Membranes," Physical Review, vol. 67, 2003, pp. 051908-1-051908-11.

Gabriel, S. et al., "The Dielectric Properties of Biological Tissues: II. Measurements in the Frequency Range 10 Hz to 20 GHZ," Physics in Medicine and Biology, vol. 41, 1996, pp. 2251-2269.

Gage, A. "Current Progress in Cryosurgery," Cryobiology 25, 1988, pp. 483-486.

Gatto, H. "Effects of Thermal Shocks on Interleukin-1 Levels and Heat Shock Protein 72 (HSP72) Expression in Normal Human Keratinocytes," PubMed, Archives of Dermatological Research, vol. 284, Issue 7, 1992: pp. 414-417 [Abstract].

Hale, H. B. et al., "Influence of Chronic Heat Exposure and Prolonged Food Deprivation on Excretion of Magnesium, Phosphorus, Calcium, Hydrogen Ion & Ketones," Aerospace Medicine, vol. 39—No. 9, Sep. 1968, pp. 919-926.

Heller Page, E. et al., "Temperature-dependent skin disorders," Journal of the American Academy of Dermatology, vol. 18, No. 5, Pt 1, May 1988, pp. 1003-1019.

Hemmingsson, A. et al. "Attenuation in Human Muscle and Fat Tissue in Vivo and in Vitro," Acra Radiologica Diagnosis, vol. 23, No. 2, 1982, pp. 149-151.

Henry, F. et al., "Les Dermatoses Hivernales," Rev Med Liege, 54:11, 1999, pp. 864-866. [Abstract Attached].

Hernan, P. et al., "Study for the evaluation of the efficacy of Lipocryolysis (EEEL)", Nov. 30, 2011.

Hernan, R. P., "A Study to Evaluate the Action of Lipocryolysis", 33(3) CryoLellers, 2012, pp. 176-180.

Holland, DB. et al. "Cold shock induces the synthesis of stress proteins in human keratinocytes," PubMed Journal of Investigative Dermatology; 101(2): Aug. 1993, pp. 196-199.

Holman, W. L. et al., "Variation in Cryolesion Penetration Due to Probe Size and Tissue Thermal Conductivity," The Annals of Thoracic Surgery, vol. 53, 1992, pp. 123-126.

(56) References Cited

OTHER PUBLICATIONS

Hong, J.S. et al., "Patterns of Ice Formation in Normal and Malignant Breast Tissue," Cryobiology 31, 1994, pp. 109-120.

Huang et al. "Comparative Proteomic Profiling of Murine Skin," Journal of Investigative Dermatology, vol. 121(1), Jul. 2003, pp. 51-64.

Isambert, H. "Understanding the Electroporation of Cells and Artificial Bilayer Membranes," Physical Review Letters, vol. 80, No. 15, 1998, pp. 3404-3707.

Jalian, H. R. et al., "Cryolipolysis: A Historical Perspective and Current Clinical Practice", 32(1) Semin. Cutan. Med. Surg., 2013, pp. 31-34.

Kellum, R. E. et al., "Sclerema Neonatorum: Report of Case and Analysis of Subcutaneous and Epidermal-Dermal Lipids by Chromatographic Methods," Archives of Dermatology, vol. 97, Apr. 1968, pp. 372-380.

Koska, J. et al., "Endocrine Regulation of Subcutaneous Fat Metabolism During Cold Exposure in Humans," Annals of the New York Academy of Sciences, vol. 967, 2002,pp. 500-505.

Kundu, S. K. et al., "Breath Acetone Analyzer: Diagnostic Tool to Monitor Dietary Fat Loss," Clinical Chemistry, vol. 39, Issue (1), 1993, pp. 87-92.

Kundu, S. K. et al., "Novel Solid-Phase Assay of Ketone Bodies in Urine," Clinical Chemistry, vol. 37, Issue (9), 1991, pp. 1565-1569.

Kuroda, S. et al. "Thermal Distribution of Radio-Frequency Inductive Hyperthermia Using an Inductive Aperture-Type Applicator: Evaluation of the Effect of Tumor Size and Depth", Medical and Biological Engineering and Computing, vol. 37, 1999, pp. 285-290.

Laugier, P. et al., "In Vivo Results with a New Device for Ultrasonic Monitoring of Pig Skin Cryosurgery: The Echographic Cryprobe," The Society for Investigative Dermatology, Inc., vol. 111, No. 2, Aug. 1998, pp. 314-319.

Levchenko et al., "Effect of Dehydration on Lipid Metabolism" Ukrainskii Biokhimicheskii Zhurnal, vol. 50, Issue 1, 1978, pp. 95-97.

Lidagoster, MD et al., "Comparison of Autologous Fat Transfer in Fresh, Refrigerated, and Frozen Specimens: An Animal Model," Annals of Plastic Surgery, vol. 44, No. 5, May 2000, pp. 512-515.

Liu, A. Y.-C et al., "Transient Cold Shock Induces the Heat Shock Response upon Recovery at 37 C in Human Cells," Journal of Biological Chemistry, , 269(20), May 20, 1994, pp. 14768-14775.

L'Vova, S.P. "Lipid Levels and Lipid Peroxidation in Frog Tissues During Hypothermia and Hibernation" Ukrainskii Biokhimicheskii Zhurnal, vol. 62, Issue 1, 1990, pp. 65-70.

Maize, J.C. "Panniculitis," Cutaneous Pathology, Chapter 13, 1998, 327-344.

Malcolm, G. T. et al., "Fatty Acid Composition of Adipose Tissue in Humans: Differences between Subcutaneous Sites," The American Journal of Clinical Nutrition, vol. 50, 1989, pp. 288-291.

Manstein, D. et al. "A Novel Cryotherapy Method of Non-invasive, Selective Lipolysis," LasersSurg.Med 40:S20, 2008, p. 104.

Manstein, D. et al. "Selective Cryolysis: A Novel Method of Non-Invasive Fat Removal," Lasers in Surgery and Medicine: The Official Journal of the ASLMS, vol. 40, No. 9, Nov. 2008, pp. 595-604.

Mayoral, "Case Reports: Skin Tightening with a Combined Unipolar and Bipolar Radiofrequency Device," Journal of Drugs in Dermatology, 2007, pp. 212-215.

Mazur, P. "Cryobiology: The Freezing of Biological Systems," Science, 68, 1970, pp. 939-949.

Merrill, T. "A Chill to the Heart: A System to Deliver Local Hypothermia Could One Day Improve the Lives of Heart-Attack Patients," Mechanical Engineering Magazine, Oct. 2010, 10 pages.

Miklavcic, D. et al. "Electroporation-Based Technologies and Treatments," The Journal of Membrane Biology (2010) 236:1-2, 2 pgs.

Moschella, S. L. et al., "Diseases of the Subcutaneous Tissue," in Dermatology, Second Edition, vol. 2, 1985 Chapter 19, Section II (W.B. Saunders Company, 1980) pp. 1169-1181.

Murphy, J. V. et al., "Frostbite: Pathogenesis and Treatment" The Journal of Trauma: Injury, Infection, and Critical Care, vol. 48, No. 1, Jan. 2000, pp. 171-178.

Nagao, T. et al., "Dietary Diacylglycerol Suppresses Accumulation of Body Fat Compared to Triacylglycerol in Men a Double-Blind Controlled Trial," The Journal of Nutrition, vol. 130, Issue (4), 2000, pp. 792-797.

Nagle, W. A. et al. "Cultured Chinese Hamster Cells Undergo Apoptosis After Exposure to Cold but Nonfreezing Temperatures," Cryobiology 27, 1990, pp. 439-451.

Nagore, E. et al., "Lipoatrophia Semicircularis-a Traumatic Panniculitis: Report of Seven Cases and Review of the Literature," Journal of the American Academy of Dermatology, vol. 39, Nov. 1998, pp. 879-881.

Nanda, G.S. et al., "Studies on electroporation of thermally and chemically treated human erythrocytes," Bioelectrochemistry and Bioenergetics, 34, 1994, pp. 129-134, 6 pgs.

Narins, D.J. et al. "Non-Surgical Radiofrequency Facelift", The Journal of Drugs in Dermatology, vol. 2, Issue 5, 2003, pp. 495-500.

Nielsen, B. "Thermoregulation in Rest and Exercise," Acta Physiologica Scandinavica Supplementum, vol. 323 (Copenhagen 1969), pp. 7-74.

Nishikawa, H. et al. "Ultrastructural Changes and Lipid Peroxidation in Rat Adipomusculocutaneous Flap Isotransplants after Normothermic Storage and Reperfusion," Transplantation, vol. 54, No. 5,1992, pp. 795-801.

Nurnberger, F. "So-Called Cellulite: An Invented Disease," Journal of Dermatologic Surgery and Oncology, Mar. 1978, pp. 221-229.

Pease, G. R. et al., "An Integrated Probe for Magnetic Resonance Imaging Monitored Skin Cryosurgery," Journal of Biomedical Engineering, vol. 117, Feb. 1995, pp. 59-63.

Pech, P. et al., "Attenuation Values, Volume Changes and Artifacts in Tissue Due to Freezing," Acta Radiologica , vol. 28, Issue 6, 1987, pp. 779-782.

Peterson, L. J. et al., "Bilateral Fat Necrosis of the Scrotum," Journal of Urology, vol. 116, 1976, pp. 825-826.

Phinney, S. D. et al., "Human Subcutaneous Adipose Tissue Shows Site-Specific Differences in Fatty Acid Composition," The American Journal of Clinical Nutrition, vol. 60, 1994, pp. 725-729.

Pierard, G.E. et al., "Cellulite: From Standing Fat Herniation to Hypodermal Stretch Marks," The American Journal of Dermatology, vol. 22, Issue 1, 2000, pp. 34-37, [Abstract].

Pope, K. et al. "Selective Fibrous Septae Heating: An Additional Mechanism of Action for Capacitively Coupled Monopolar Radiofrequency" Thermage, Inc. Article, Feb. 2005, 6pgs.

Quinn, P. J. "A Lipid-Phase Separation Model of Low-Temperature Damage to Biological Membranes," Cryobiology, 22, 1985, 128-146.

Rabi, T. et al., "Metabolic Adaptations in Brown Adipose Tissue of the Hamster in Extreme Ambient Temperatures," American Journal of Physiology, vol. 231, Issue 1, Jul. 1976, pp. 153-160.

Renold, A.E. et al. "Adipose Tissue" in Handbook of Physiology, Chapter 15, (Washington, D.C., 1965) pp. 169-176.

Rossi, A. B. R. et al. "Cellulite: a Review," European Academy of Dermatology and Venercology, 2000, pp. 251-262, 12 pgs.

Rubinsky, B. "Principles of Low Temperature Cell Preservation," Heart Failure Reviews, vol. 8, 2003, pp. 277-284.

Rubinsky, B. et al., "Cryosurgery: Advances in the Application of low Temperatures to Medicine," International Journal of Refrigeration, vol. 14, Jul. 1991, pp. 190-199.

Saleh, K.Y. et al., "Two-Dimensional Ultrasound Phased Array Design for Tissue Ablation for Treatment of Benign Prostatic Hyperplasia," International Journal of Hyperthermia, vol. 20, No. 1, Feb. 2004, pp. 7-31.

Schoning, P. et al., "Experimental Frostbite: Freezing Times, Rewarming Times, and Lowest Temperatures of Pig Skin Exposed to Chilled Air," Cryobiology 27, 1990, pp. 189-193.

Shephard, R. J. "Adaptation to Exercise in the Cold," Sports Medicine, vol. 2, 1985, pp. 59-71.

Sigma-Aldrich "Poly(ethylene glycol) and Poly(ethylene oxide)," http://www.sigmaaldrich.com/materials-science/materialscience-;products.htmi?TablePage=2020411 0, accessed Oct. 19, 2012.

(56) References Cited

OTHER PUBLICATIONS

Smalls, L. K. et al. "Quantitative Model of Cellulite: Three Dimensional Skin Surface Topography, Biophysical Characterization, and Relationship to Human Perception," International Journal of Cosmetic Science, vol. 27, Issue 5, Oct. 2005, 17 pgs.
Thermage, News Release, "Study Published in Facial Plastic Surgery Journal Finds Selective Heating of Fibrous Septae Key to Success and Safety of Thermage ThermaCool System," Jun. 20, 2005, 2 pages.
"ThermaCool Monopolar Capacitive Radiofrequency, the one choice for nonablative tissue tightening and contouring", Thermage, Inc. Tech Brochure, Nov. 30, 2005, 8 pgs.
Vallerand et al. "Cold Stress Increases Lipolysis, FFA Ra and TG/FFA Cycling in Humans," Aviation, Space, and Environmental Medicine 70(1), 1999, pp. 42-50.
Wang, X. et al., "Cryopreservation of Cell/Hydrogel Constructs Based on a new Cell-Assembling Technique," Sep. 5, 2009, 40 pages.
Wharton, D. A. et al., "Cold Acclimation and Cryoprotectants in a Freeze-Tolerant Antarctic Nematode, Panagrolaimus Davidi,", Journal of Comparative Physiology, vol. 170, No. 4, Mar. 2000, 2 pages.
Winkler, C. et al., "Gene Transfer in Laboratory Fish: Model Organisms for the Analysis of Gene Function," in Transgenic Animals, Generation and Use (The Netherlands 1997), pp. 387-395.
Young, H. E. et al. "Isolation of Embryonic Chick Myosatellite and Pluripotent Stem Cells" The Journal of Tissue Culture Methods, vol. 14, Issue 2, 1992, pp. 85-92.
Zelickson, B. et al., "Cryolipolysis for Noninvasive Fat Cell Destruction: Initial Results from a Pig Model", 35 Dermatol. Sug., 2009, pp. 1-9.
Zouboulis, C. C. et al., "Current Developments and Uses of Cryosurgery in the Treatment of Keloids and Hypertrophic Scars," Wound Repair and Regeneration, vol. 10, No. 2, 2002, pp. 98-102.
European Search Report, European Patent Application No. EP 07761461.8; Applicant: Zeltiq Aesthetics, Inc., Mailing Date: Apr. 25, 2012, 9 pages.
International Search Report and Written Opinion for PCT/US2007/067638; Applicant: Juniper Medical, Inc.; Date of Mailing: Jan. 10, 2008, 11 pages.
Brazilian Examination Report for Brazilian Application No. PI 0706055-6; Applicant Zeltiq Aesthetics, Inc.; Date of Mailing: Nov. 19, 2019, 18 pages.
U.S. Appl. No. 13/747,161, filed Jan. 22, 2013, obtained Feb. 11, 2020; 483 pages.
Gao, D. "A Study of Physical and Biological Mechanisms of Cryoinjury and Cryoprotection of Human Erythrocytes in Freezing Preservation" Department of Mechanical Engineering Thesis, Concordia University, Mar. 1991. 253 pages.
Disclosure re: "Method and Apparatus for Regional Fat Reduction Using Controlled and Sustained Cooling of Skin Surface." Oct. 12, 2006. 7 pages.
Beise, R.D. et al. (Jan. 1, 1998). "Psychophysical study of stinging pain evoked by brief freezing of superficial skin and ensuing short-lasting changes in sensations of cool and cold pain." Pain, vol. 74, Jan. 1, 1998 (Jan. 1, 1998), pp. 275-286, XP055620108, DOI: 10.1016/S0304-3959(97)00179-6.
Cohen, ML. (1977). "Measurement of The Thermal Properties of Human Skin. A review." J. Invest. Dermatol., 69, pp. 333-338.
Golstein, P. et al. (2007). "Cell death by necrosis: Towards a molecular definition." Trends Biochem Sci. 32:1 37-43.
Petersen, A., et al. "A new approach for freezing of aqueous solutions under active control of the nucleation temperature", Cryobiology 53 (2006) 248-257.
Vuraki, K.A. et al. (1989). "A device for cryovacuum treatment." Med tech, Jan.-Feb. 1989, (1):46-9 (extracted from PUBMED on Dec. 6, 2016). English translation. 7 pages.

\* cited by examiner

CRYOPROTECTANT FOR USE WITH A TREATMENT DEVICE FOR IMPROVED COOLING OF SUBCUTANEOUS LIPID-RICH CELLS

CROSS-REFERENCE TO RELATED APPLICATION(S)

The present application is a continuation of U.S. patent application Ser. No. 13/747,161, filed on Jan. 22, 2013, which is a continuation of U.S. patent application Ser. No. 11/741.271, filed on Apr. 27, 2007, which claims the benefit and priority to U.S. Provisional Patent Application No. 60/795,799, filed on Apr. 28, 2006, the entireties of each of the foregoing which are incorporated herein by reference.

BACKGROUND

Excess body fat, or adipose tissue, can detract from personal appearance and athletic performance. Excess adipose tissue may be present in various locations of the body, including, for example, the thigh, buttocks, abdomen, knees, back, face, arms, and other areas. Moreover, excess adipose tissue is thought to magnify the unattractive appearance of cellulite, which forms when subcutaneous fat protrudes into the dermis and creates dimples where the skin is attached to underlying structural fibrous strands. Cellulite and excessive amounts of adipose tissue are often considered to be unappealing. Moreover, significant health risks may be associated with higher amounts of excess body fat. An effective way of controlling or removing excess body fat therefore is needed.

Liposuction is a method for selectively removing adipose tissue to "sculpt" a person's body. Liposuction typically is performed by plastic surgeons or dermatologists using specialized surgical equipment that invasively removes subcutaneous adipose tissue via suction. One drawback of liposuction is that it is a surgical procedure, and the recovery may be painful and lengthy. Moreover, the procedure typically requires the injection of tumescent anesthetics, which is often associated temporary bruising. Liposuction can also have serious and occasionally even fatal complications. In addition, the cost for liposuction is usually substantial. Other emerging techniques for removal of subcutaneous adipose tissue include mesotherapy, laser-assisted liposuction, and high intensity focused ultrasound.

Conventional non-invasive treatments for removing excess body fat typically include topical agents, weight-loss drugs, regular exercise, dieting, or a combination of these treatments. One drawback of these treatments is that they may not be effective or even possible under certain circumstances. For example, when a person is physically injured or ill, regular exercise may not be an option. Similarly, weight-loss drugs or topical agents are not an option when they cause an allergic or negative reaction. Furthermore, fat loss in selective areas of a person's body cannot be achieved using general or systemic weight-loss methods.

Other non-invasive treatment methods include applying heat to a zone of subcutaneous lipid-rich cells. U.S. Pat. No. 5,948,011 discloses altering subcutaneous body fat and/or collagen by heating the subcutaneous fat layer with radiant energy while cooling the surface of the skin. The applied heat denatures fibrous septae made of collagen tissue and may destroy fat cells below the skin, and the cooling protects the epidermis from thermal damage. This method is less invasive than liposuction, but it still may cause thermal damage to adjacent tissue, and can also be painful and unpredictable.

Another promising method of reducing subcutaneous fat cells is to cool the target cells as disclosed in U.S. Patent Publication No. 2003/0220674, the entire disclosure of which is incorporated herein. This publication discloses, among other things, reducing the temperature of lipid-rich subcutaneous fat cells to selectively affect the fat cells without damaging the cells in the epidermis. Although this publication provides promising methods and devices, several improvements for enhancing the implementation of these methods and devices would be desirable.

U.S. Patent Publication No. 2003/0220674 also discloses methods for selective removal of lipid-rich cells, and avoidance of damage to other structures including dermal and epidermal cells. A method for inducing collagen compaction, remodeling, and formation is also needed for treatment of loose or sagging skin, age- or sun-damaged skin, or a variety of other skin disorders. Therefore, a method for simultaneously removing lipid-rich cells while providing beneficial collagen effects is also needed.

DETAILED DESCRIPTION

A. OVERVIEW

The present disclosure describes devices, systems, and methods for cooling subcutaneous lipid-rich cells with a heat exchanging element and a thermally conductive cryoprotectant. The term "subcutaneous tissue" means tissue lying beneath the dermis and includes subcutaneous fat, or adipose tissue, which primarily is composed of lipid-rich cells, or adipocytes. It may be appreciated that several of the details set forth below are provided to describe the following embodiments in a manner sufficient to enable a person skilled in the relevant art to make and use the disclosed embodiments. Several of the details and advantages described below, however, may not be necessary to practice certain embodiments of the invention. Additionally, the invention may include other embodiments that are within the scope of the claims but are not described in detail with respect to the Figures.

B. SYSTEM FOR SELECTIVELY REDUCING LIPID-RICH CELLS

Figure 1:
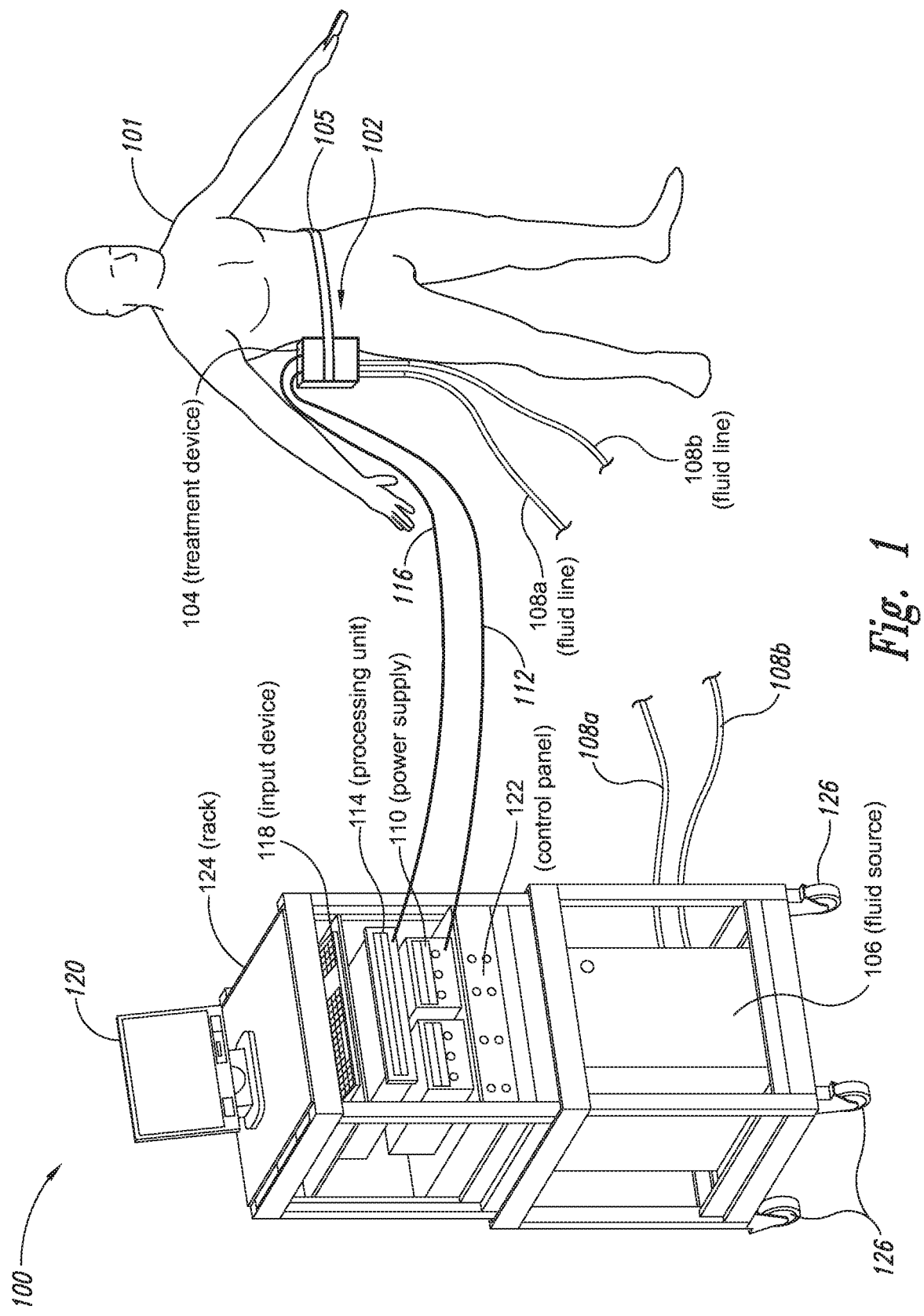
FIG. 1 is an isometric view of a system for removing heat from subcutaneous lipid-rich cells in accordance with an embodiment of the invention.

FIG. 1 is an isometric view of a treatment system 100 for exchanging heat from subcutaneous lipid-rich cells of a subject 101 in accordance with an embodiment of the invention. The treatment system 100 may include a treatment device 104 placed at an abdominal area 102 of the subject 101 or another area where reduction of the subcutaneous fat, or fat layer, is desired. The treatment device 104 may be fastened to the subject 101 using, for example, a mechanical fastener (e.g., a belt 105), an adhesive (e.g., an epoxy), suction (e.g., a vacuum or reduced pressure), or any other mechanisms. The treatment device 104 may be configured to heat and/or cool the subject 101. In certain embodiments, the treatment device 104 may contain a non-freezing cryoprotectant to, among other advantages, allow pre-cooling of the treatment device 104 to a temperature around or below the freezing point of water (0° C.) while preventing ice from forming. Various embodiments of the treatment device 104 are described in more detail below with reference to FIGS. 7-10. In other embodiments, the treatment system 100 may also include a coupling device (not shown in FIG. 1) for supplying the cryoprotectant to the treatment device 104 or the skin of the subject 101, as described in more detail below with reference to FIG. 2 and FIG. 3.

In one embodiment, the treatment device 104 is configured to cool subcutaneous lipid-rich cells of the subject 101. In such cases, the treatment system 100 may further include a fluid source 106 and fluid lines 108a-b connecting the treatment device 104 to the fluid source 106. The fluid source 106 may remove heat from a coolant to a heat sink and provide the chilled coolant to the treatment device 104 via the fluid lines 108a-b. Examples of the circulating coolant include water, glycol, synthetic heat transfer fluid, oil, a refrigerant, and any other suitable heat conducting fluids. The fluid lines 108a-b may be hoses or other conduits constructed from polyethylene, polyvinyl chloride, polyurethane, steel, aluminum, copper and other materials that may accommodate the particular circulating coolant. The fluid source 106 may be a refrigeration unit, a cooling tower, a thermoelectric chiller, or any other device capable of removing heat from a coolant or municipal water supply.

The treatment device 104 may also include one or more thermoelectric elements, such as Peltier-type thermoelectric elements. In such cases, the treatment system 100 may further include a power supply 110 and a processing unit 114 operatively coupled to the treatment device 104 via electrical cables 112, 116. In one embodiment, the power supply 110 may provide a direct current voltage to the treatment device 104 remove heat from the subject 101. The processing unit 114 may monitor process parameters via sensors (not shown in FIG. 1) placed proximate to the treatment device 104 and adjust the heat removal rate based on the process parameters. The processing unit 114 may include any processor, Programmable Logic Controller, Distributed Control System, and the like.

The processing unit 114 may be in electrical communication with an input device 118, an output device 120, and/or a control panel 122. The input device 118 may include a keyboard, a mouse, a touch screen, a push button, a switch, a potentiometer, and any other device suitable for accepting user input. The output device 120 may include a display screen, a printer, a medium reader, an audio device, and any other device suitable for providing user feedback. The control panel 122 may include indicator lights, numerical displays, and audio devices. In the embodiment shown in FIG. 1, the processing unit 114, power supply 110, control panel 122, fluid source 106, input device 118, and output device 120 are carried by a rack 124 with wheels 126 for portability. In another embodiment, the various components may be fixedly installed at a treatment site.

As explained in more detail below, a cryoprotectant applied to the treatment device 104 may allow the treatment device 104 to be pre-cooled prior to being applied to the subject 101 for more efficient treatment. Further, the cryoprotectant can also enable the treatment device 104 to be maintained at a desired temperature while preventing ice from forming on a surface of the treatment device 104, and thus reduces the delay in reapplying the treatment device 104 to the subject. Yet another advantage is that the cryoprotectant may prevent the treatment device 104 from freezing to the skin of the subject. If the cryoprotectant is hygroscopic, it can adsorb moisture from the atmosphere and/or from the skin, which might otherwise form ice.

The treatment device 104, the cryoprotectant, and/or other components of the treatment system 100 can be included in a kit (not shown) for removing heat from subcutaneous lipid rich cells of the subject 101. The cryoprotectant can have a freezing point in the range of about −40° C. to about 0° C. and be configured to be applied to an interface between the treatment device 104 and the skin of the subject 101. The kit can also include instruction documentation containing information regarding how to (a) apply the cryoprotectant to a target region and/or a heat exchanging surface of the treatment device 104 and (b) reduce a temperature of the target region such that lipid rich cells in the region are affected while preserving non-lipid rich cells proximate to the heat exchanging surface.

C. COUPLING DEVICE

Figure 2:
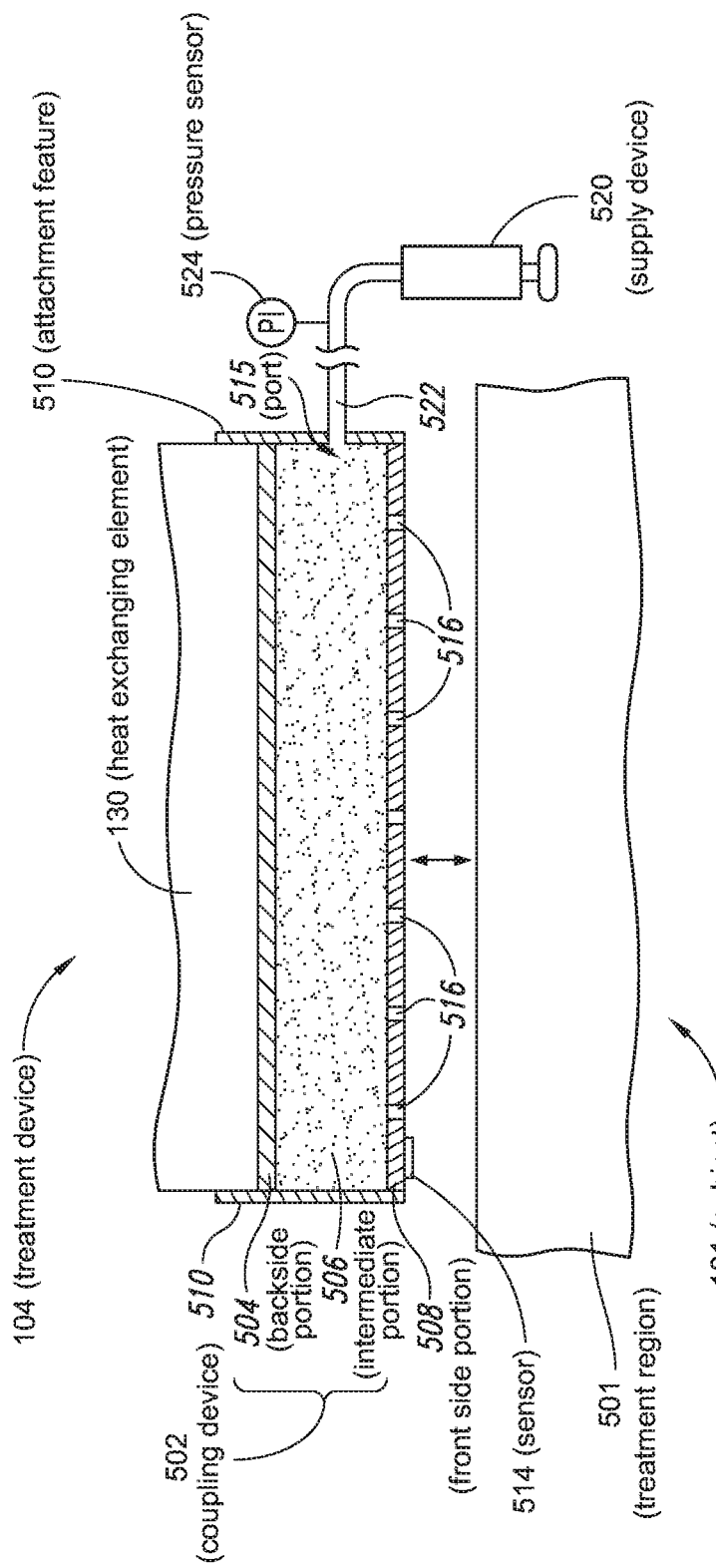
FIG. 2 is a side elevation view of a coupling device in accordance with an embodiment of the invention.

FIG. 2 is a side elevation view illustrating a coupling device 502 suitable to be used in the treatment system 100 of FIG. 1 and configured in accordance with an embodiment of the invention. The coupling device 502 may be placed adjacent to a treatment region 501 of the subject 101. The coupling device 502 may include attachment features 510 for releasably or fixedly attaching the coupling device 502 to a heat exchanging element 130 of the treatment device 104 (FIG. 1). In the illustrated embodiment, the attachment features 510 include tensioning clips. During assembly, the coupling device 502 may be snapped onto the heat exchanging element 130 with the backside portion 504 facing the treatment device 104. In other embodiments, the attachment features 510 may include screws, pins, hinges, and/or any other suitable attachment devices.

The coupling device 502 may include a backside portion 504 proximate to the heat exchanging element 130, a front side portion 508 spaced apart from the backside portion 504, and an intermediate portion 506 between the backside portion 504 and the front side portion 508. In certain embodiments, the coupling device 502 optionally may include a protective layer (e.g., a polymeric film, not shown)

attached to the front side portion 508. The protective layer may isolate the front side portion 508 from the environment and may be peeled off to expose the front side portion 508 before treatment.

The backside portion 504 may be a film, a plate, a sheet, or other structure constructed from a metal, a metal alloy, ceramics, a polymeric material, or other suitable conductive material. The backside portion 504 may transfer heat between the heat exchanging element 130 and the treatment region 501. The backside portion 504 may also isolate the heat exchanging element 130 from the treatment region 501 for sanitation purposes.

The intermediate portion 506 may be a reservoir constructed from a mesh, a foam material, a porous plastic and/or metal, or other materials that may at least temporarily contain a fluid and/or a gel. In one embodiment, the intermediate portion 506 contains, or is loaded with, a cryoprotectant before a treatment process begins. In another embodiment, the intermediate portion 506 may be generally empty before a treatment process begins and only loaded with cryoprotectant immediately before and/or during the treatment process. In any of these embodiments, the intermediate portion 506 may be pressurized with the cryoprotectant or may be at a generally atmospheric pressure during treatment.

The front side portion 508 may be a film constructed from a polymeric material, a plastic material, or other material that is at least partially flexible. The front side portion 508 may include one or more apertures 516 in fluid communication with the intermediate portion 506. During treatment, the aperture or apertures 516 may allow the cryoprotectant contained in the intermediate portion 506 to escape to the treatment region 501 of the subject 101 through capillary actions or other mechanisms. For example, the intermediate portion 506 may continually supply the cryoprotectant to the treatment region 501 during treatment. In certain embodiments, the intermediate portion 506 is pre-loaded with excess cryoprotectant. As a portion of the cryoprotectant escapes from the apertures 516, additional cryoprotectant may be supplied from the intermediate portion 506 to the skin of the subject during treatment. In other embodiments, the intermediate portion 506 may be constantly replenished to provide a continuous supply of the cryoprotectant. The cryoprotectant can be absorbed by the skin in the treatment region 501. The degree of cryoprotectant absorption by the skin depends on a number of factors, the most important of which are cryoprotectant concentration, duration of contact, solubility, and the physical condition of the skin.

The coupling device 502 optionally may include at least one sensor 514 proximate to the front side portion 508 to measure at least one parameter of the treatment process. The sensor 514 may be a temperature sensor, a pressure sensor, a transmissivity sensor, a bio-resistance sensor, an ultrasound sensor, an optical sensor, an infrared sensor, a heat flux sensor, any other desired sensors, or any combination thereof. An operator may adjust the treatment process based on the measured parameter.

In the illustrated embodiment, the treatment device 104 optionally may include a supply device 520 connected to a port 515 of the coupling device 502 by a conduit 522 for supplying and/or replenishing the cryoprotectant in the intermediate portion 506. In the illustrated embodiment, the supply device 520 is a syringe holding a volume of the cryoprotectant. In other embodiments, the supply device 520 may include a pump coupled to a cryoprotectant storage (not shown), or other suitable supply configurations.

Optionally, a pressure sensor 524 (shown schematically) may be used for monitoring a cryoprotectant pressure in the intermediate portion 506. The pressure sensor 524 may be operatively coupled to the conduit 522, the intermediate portion 506, or the supply device 520. During treatment, the pressure sensor 524 may provide an electric, visual, or other signal indicating the cryoprotectant pressure in the intermediate portion 506. In one embodiment, an operator may manually adjust the output of the supply device 520 based on the indicated pressure. In another embodiment, the signal from the pressure sensor 524 may be used as a process variable to automatically control the output of the supply device 520.

Several embodiments of the treatment system 100 may continually protect the skin of the subject against freezing damage. According to conventional techniques, a cryoprotectant may be topically applied to the skin before a treatment begins. The skin then absorbs the applied cryoprotectant, which dissipates over a period of time. After the cryoprotectant dissipates, in conventional techniques, the skin may be subject to freezing damage. As a result, by continually replenishing the dissipated cryoprotectant from the intermediate portion 506, the treatment system 100 may at least reduce the risk of freezing damage, or even prevent such freezing damage, during treatment.

Several embodiments of the treatment system 100 may also reduce the risk of air pockets that can reduce the heat transfer efficiency between the treatment region 501 and the treatment device 104. As the cryoprotectant escapes through the aperture or apertures 516 during treatment, the pressure in the intermediate portion 506 decreases, and air pockets may form. The air pockets may interfere with the heat transfer efficiency between the treatment region 501 and the treatment device 104. As a result, maintaining the intermediate portion 506 at a constant pressure may at least reduce the risk of air pocket formation, and thus improve the efficiency of such heat transfer.

Figure 3:
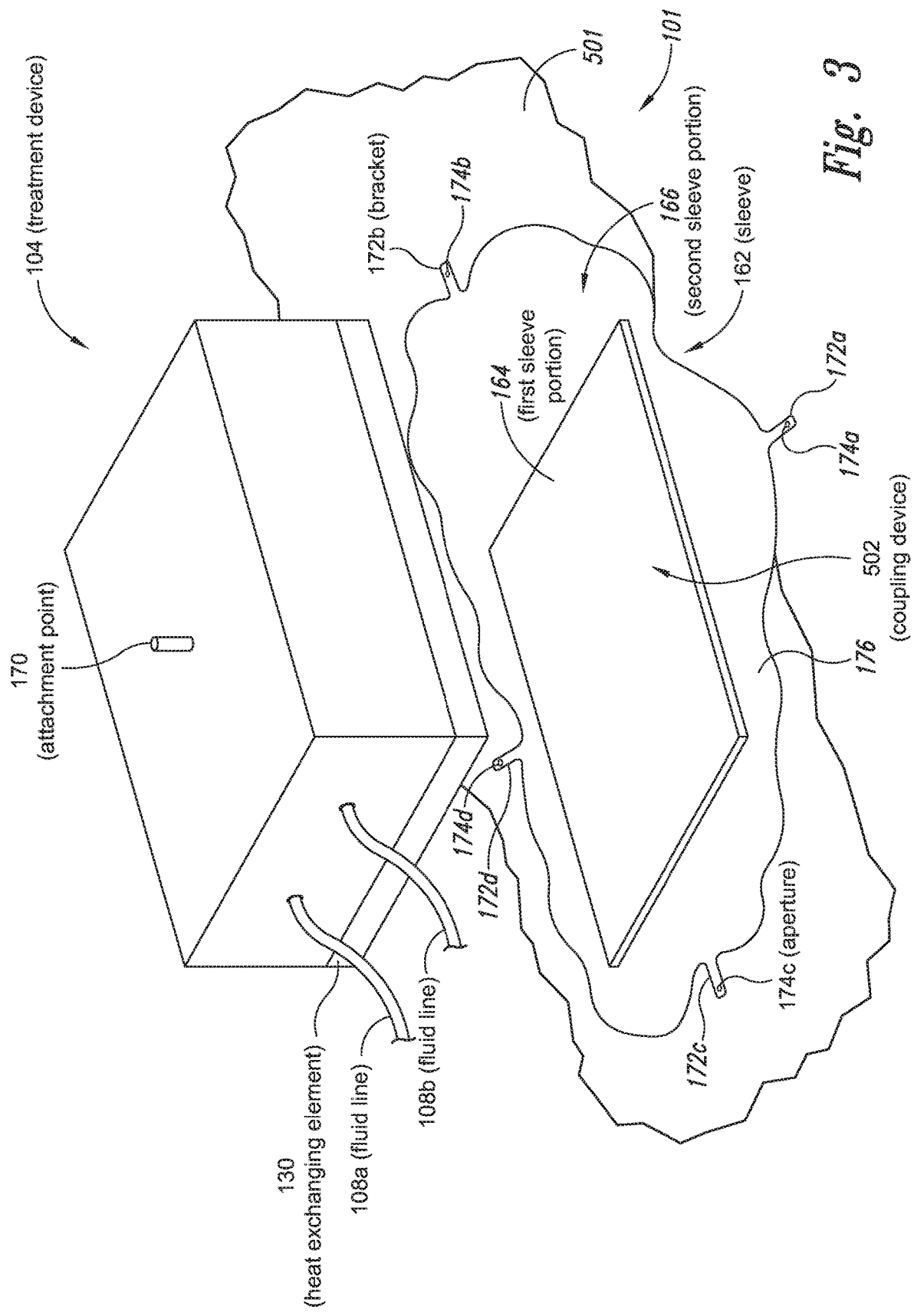
FIG. 3 is an isometric view of a coupling device in accordance with another embodiment of the invention.

Even though the coupling device 502 is illustrated as having the attachment features 510, in certain embodiments, the attachment features 510 may be omitted, and the coupling device 502 may be configured and/or incorporated into other structures. For example, FIG. 3 illustrates another embodiment, in which the coupling device 502 is incorporated into a sleeve 162 that attaches to the heat exchanging element 130. The coupling device 502 can define a first sleeve portion 164, and the sleeve 162 can also have a second sleeve portion 166. For example, the first sleeve portion 164 may include the backside portion 504, the front side portion 508, and the intermediate portion 506 (FIG. 3). The second sleeve portion 166 may be an isolation layer extending from the first sleeve portion 164. For example, the second sleeve portion 166 may be constructed from latex, rubber, nylon, polyimide, polyethylene, Kevlar®, or other substantially impermeable or semi-permeable material. The second sleeve portion 166 may prevent any contact between the skin of the subject and the heat exchanging element 130. In one embodiment, the sleeve 162 may be reusable. In other embodiments, the sleeve 162 may be disposable. The sleeve 162 may be provided sterile or non-sterile. In one embodiment, the sleeve is fabricated from a flex circuit material such as polyimide or polyethylene, with etched traces to connect sensors to electronics resident in, e.g., the processing unit 114.

The second sleeve portion 166 may also include attachment features to affix the sleeve 162 to the treatment device 104. In the illustrated embodiment, the second sleeve portion 166 includes four brackets 172 (identified individually as 172a-d), each located at a corner of the second sleeve portion 166. Individual brackets 172 include an aperture 174 (identified individually as 174a-d) that corresponds to an attachment point 170 of the treatment device 104. During assembly, the apertures 174 of the brackets 172 may fit over the attachment point 170 such that the second sleeve portion 166 at least partially encloses the heat exchanging element 130.

In another embodiment, the second sleeve portion 166 may include brackets that may engage each other. For example, the bracket 172a may include a pin that may engage the aperture 174d of the bracket 172d. During assembly, the second sleeve portion 166 may wrap around the treatment device 104 and be held in place by engaging the brackets 172 with each other. In a further embodiment, the second sleeve portion 166 may include a flexible member (not shown, e.g., an elastic band) at an outer edge 176 of the second sleeve portion 166 that may hold the sleeve 162 over the treatment device 104 during assembly. In a further embodiment, the second sleeve portion 166 may include a releasable attachment member (not shown, e.g., Velcro® or snaps) at the outer edge 176 of the second sleeve portion 166 that may hold the sleeve 162 over the treatment device 104 during assembly. In yet another embodiment, adhesive may hold the second sleeve portion 166 to the treatment device 104.

In addition to the expected advantages described above, one expected advantage of using the sleeve 162 is the improved sanitation of using the treatment device 104. The sleeve 162 may prevent cross-contamination between the skin of the subject and the heat exchanging element 130 because the sleeve 162 is substantially impermeable. Also, operating expense of the treatment device 104 may be reduced because the heat exchanging element 130 does not need to be sanitized after each use.

The sleeve 162 may have many additional embodiments with different and/or additional features without detracting from its operation. For example, the first and second sleeve portions 164, 166 may be constructed from the same material (e.g., polyimide) or different materials. The sleeve 162 may include an adhesive layer (not shown) that binds the sleeve 162 to the treatment device 104.

D. METHOD OF PRE-COOLING A TREATMENT DEVICE USING A CRYOPROTECTANT

Figure 4:
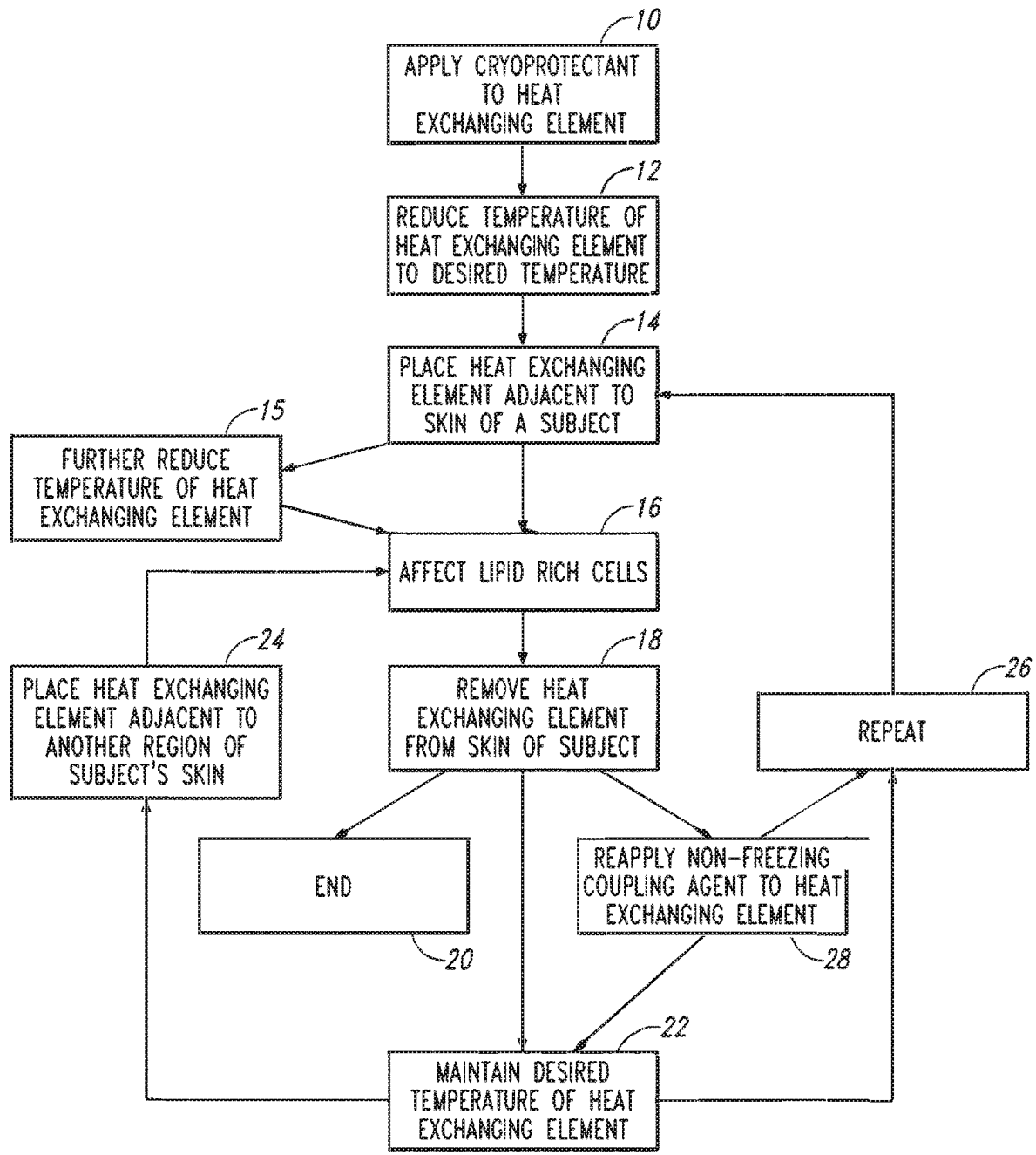
FIG. 4 is a flow chart illustrating a method for pre-cooling a treatment device in accordance with embodiments of the invention.

FIG. 4 is a flow chart illustrating a method suitable to be performed in the treatment system 100 of FIG. 1 and in accordance with an embodiment of the invention. The method may include applying a cryoprotectant to a heat exchanging element contained in a treatment device (block 10). In certain embodiments, the cryoprotectant may be applied to the skin of a subject or both the skin and the heat exchanging element. The temperature of the heat exchanging element may be reduced to a desired temperature (block 12). Once the temperature of the heat exchanging element is reduced to a desired temperature, for example, around or below the freezing point of water (0° C.), the heat exchanging element may be placed adjacent to the skin of a subject (block 14). Placing the heat exchanging element adjacent to the skin of a subject reduces the temperature of a region such that lipid-rich cells in the region are selectively affected while non-lipid-rich cells in the epidermis and/or dermis are not generally affected (block 16). In certain embodiments, the temperature of the treatment device optionally may be further reduced to a treatment temperature once the heat exchanging element is placed adjacent to the skin of a subject (block 15).

After a selected period of time, the treatment device may then be removed from the skin of the subject (block 18), and the process may then end (block 20). Once the treatment device is removed from the skin of the subject, the reduced temperature of the heat exchanging element optionally may be maintained at a desired temperature (block 22). In certain embodiments, the heat exchanging element optionally may be placed adjacent to another region of the skin of the subject to selectively affect lipid-rich cells in a different region of the skin of the subject (block 24). Once the heat exchanging element is placed adjacent to another region of the skin of the subject, the lipid-rich cells are affected (block 16). The treatment device may then be removed from the skin of the subject (block 18) and then the process may end (block 20). Optionally, the cryoprotectant may be reapplied to the heat exchanging element, the skin of the subject, or to an interface between the treatment device and the skin of the subject (block 28) prior to placing the heat exchanging element on another region of the skin of the subject.

In another embodiment, a cryoprotectant may be applied to the heat exchanging element, the skin of the subject, or an interface between the treatment device and the skin of the subject to prevent the formation of ice (block 10) as the temperature of the heat exchanging element is reduced to a desired temperature. The heat exchanging element is placed adjacent to the skin of the subject in a desired region (block 14), and the lipid-rich cells are selectively affected (block 16). After a selected period of time, the heat exchanging element may then be removed from the skin of the subject (block 18). Optionally, the cryoprotectant is reapplied to the heat exchanging element, the skin of the subject, and/or an interface between the treatment device and the skin of the subject (block 28), and the temperature of the heat exchanging element is maintained at a desired temperature (block 22). The process of treating the selected region of the skin of the subject optionally may be repeated to selectively affect the lipid-rich cells in a region of the subject while non-lipid-rich cells in the epidermis and/or dermis are not generally affected (block 26).

Figure 5:
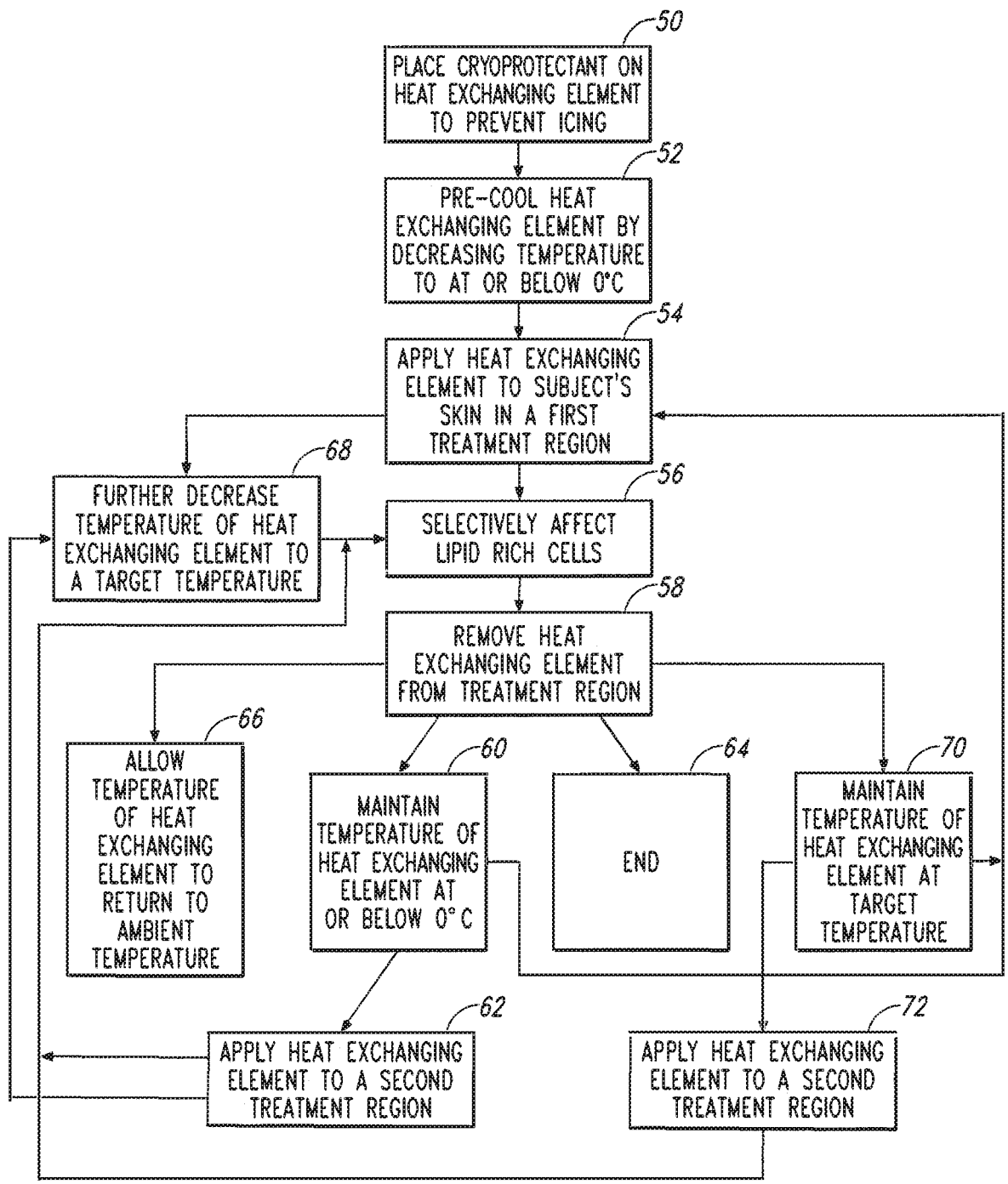
FIG. 5 is a flow chart illustrating a method for pre-cooling a treatment device in accordance with further embodiments of the invention.

FIG. 5 illustrates another method for pre-cooling the heat exchanging element by applying a cryoprotectant on the heat exchanging element prior to decreasing the temperature of the heat exchanging element to prevent icing. In one embodiment, a cryoprotectant is placed on the heat exchanging element to prevent the heat exchanging element from icing (block 50). The heat exchanging element is then pre-cooled by decreasing the temperature to at or below 0° C. (block 52). The heat exchanging element is applied to the skin of the subject in a first treatment region (block 54), to selectively affect lipid-rich cells in the treatment region (block 56). In certain embodiments, the temperature of the heat exchanging element may be further decreased (block 68). The heat exchanging element is then removed from the treatment region (block 58) and the treatment may then end (block 64). In certain embodiments, the temperature of the heat exchanging element may be maintained at a target temperature (block 60), and the heat exchanging element may be applied to a second treatment region on the skin of the subject (block 62), to selectively affect the lipid-rich cells. Once the heat exchanging element is removed from the treatment region (block 58), the temperature of the heat exchanging element may be allowed to return to an ambient temperature (block 66), or the temperature of the heat exchanging element may be maintained at or below 0° C.

(block 60). In yet another embodiment, the temperature of the heat exchanging element may be maintained at a target temperature (block 70). The heat exchanging element may then be applied to a second treatment region on the skin of the subject (block 72), or may be reapplied to the first treatment region on the skin of the subject to selectively affect the lipid-rich cells (block 54).

By cooling the subcutaneous tissues to a temperature lower than 37° C., subcutaneous lipid-rich cells may be selectively affected. In general, the epidermis and dermis of a subject have lower amounts of unsaturated fatty acids compared to the underlying lipid-rich cells forming the subcutaneous tissues. Because non-lipid-rich cells usually withstand colder temperatures better than lipid-rich cells, the subcutaneous lipid-rich cells may be selectively affected while maintaining the non-lipid-rich cells in the dermis and epidermis. For example, a range for the heat exchanging elements may be from about −20° C. to about 20° C., preferably from about −20° C. to about 10° C., more preferably from about −15° C. to about 5° C., more preferably from about −10° C. to about 0° C.

The lipid-rich cells may be affected by affecting, shrinking, disabling, destroying, removing, killing, or otherwise being altered. Without being bound by theory, selectively affecting lipid-rich cells is believed to result from localized crystallization of highly saturated fatty acids at temperatures that do not induce crystallization in non-lipid-rich cells. The crystals may rupture the bi-lipid membrane of lipid-rich cells to selectively necrose these cells. Thus, damage of non-lipid-rich cells, such as dermal cells, may be avoided at temperatures that induce crystal formation in lipid-rich cells. Cooling is also believed to induce lipolysis (e.g., fat metabolism) of lipid-rich cells to further enhance the reduction in subcutaneous lipid-rich cells. Lipolysis may be enhanced by local cold exposure, inducing stimulation of the sympathetic nervous system.

One expected advantage of several of the embodiments described above is that the treatment device may selectively reduce subcutaneous lipid-rich cells without unacceptably affecting the dermis, epidermis, and/or other tissues. Another expected advantage is that the treatment device may simultaneously selectively reduce subcutaneous lipid-rich cells while providing beneficial effects to the dermis and/or epidermis. These effects may include: fibroplasias, neocollagenesis, collagen contraction, collagen compaction, collagen density increase, collagen remodeling, and acanthosis (epidermal thickening).

Another expected advantage of several of the embodiments described above is that the heat exchanging element may be pre-cooled in advance of treatment to more efficiently treat the skin of the subject. Further, the embodiments allow the treatment device to be maintained at a temperature at or below 0° C. or at a target temperature because the cryoprotectant may prevent icing on the heat exchanging element and/or on the skin of the subject.

E. METHOD OF PROTECTING THE SKIN OF A SUBJECT USING CRYOPROTECTANT

Figure 6:
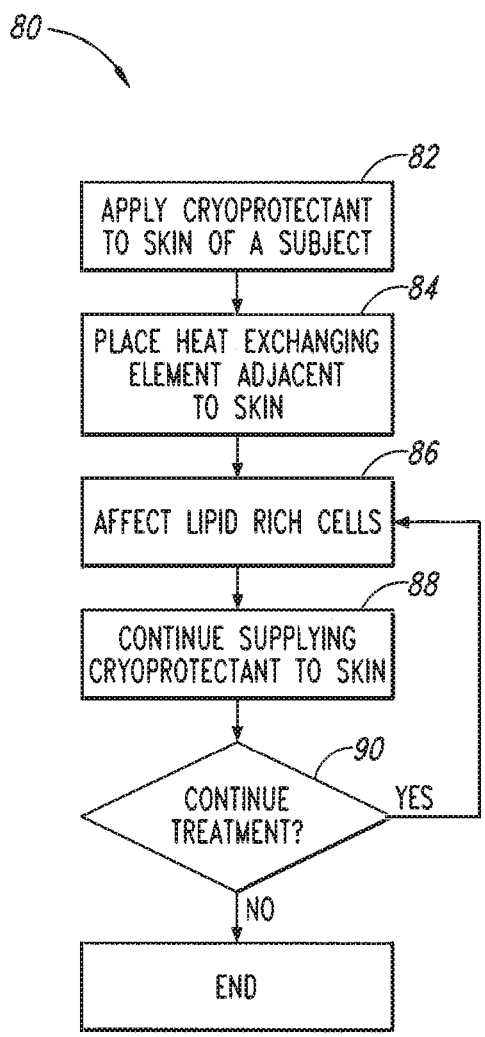
FIG. 6 is a flow chart illustrating a method for protecting the skin of a subject with a cryoprotectant in accordance with further embodiments of the invention.

FIG. 6 is a flow chart illustrating another method suitable to be performed in the treatment system 100 of FIG. 1 and in accordance with an embodiment of the invention. The method 80 of FIG. 6 may be applied separately or in combination with the methods shown in FIG. 4 and/or FIG. 5. For example, a cryoprotectant may be applied to both the skin of the subject for protecting the skin from freezing damage and the heat exchanging surface of the treatment device for pre-cooling the treatment device.

In the illustrated embodiment, the method 80 may include applying a cryoprotectant to a treatment region of the skin of the subject (block 82). For example, applying the cryoprotectant may include spraying or smearing the cryoprotectant onto the skin using an instrument including, e.g., a spatula, a spray bottle, and/or a coupling device as shown in FIG. 2. In another embodiment, the cryoprotectant may be injected into the skin of the subject using, e.g., a syringe.

A heat exchanging element is subsequently placed adjacent to the skin of the subject (block 84). The heat exchanging element may cool the treatment region that is in contact with the cryoprotectant to selectively affect lipid-rich cells in the region (block 86). During treatment, the cryoprotectant may be continually supplied to the skin of the subject (block 88). The continually supplied cryoprotectant may maintain a sufficient concentration of absorbed cryoprotectant in the epidermis and/or dermis of the subject for reducing the risk of freezing damage. The cryoprotectant may be continually supplied using an absorbent (e.g., a cotton pad, a gauze, or other absorbents) pre-loaded with the cryoprotectant, or using a coupling device releasably attached to the treatment device.

A decision is made to determine whether the treatment should be continued (block 90). The determination may be based on time, skin temperatures, and/or other parameters of the treatment process. If the treatment is continued, then the process returns to block 86; otherwise, the process ends.

The applied cryoprotectant may at least reduce the risk of freezing damage in the epidermis and/or dermis of the subject during treatment and may even prevent such freezing damage. Without being bound by theory, it is believed that low temperatures may potentially cause damage in the epidermis and/or dermis via at least intracellular and/or extracellular ice formation. Intracellular ice formation occurs when ice forms inside a cell. The ice may expand and rupture the cell as the ice grows through the cellular wall, thus causing cell death. When extracellular ice formation occurs, extracellular water freezes to form ice. As a result, the remaining extracellular fluid becomes concentrated with solutes. The high concentration of the extracellular fluid may cause intracellular fluid to permeate through the semi-permeable cellular wall and eventually cause cell dehydration and death. The high concentration of the extracellular fluid may also interrupt electrical and/or ionic interactions among neighboring cells to cause irreversible protein damage.

Applying a cryoprotectant may at least reduce the risk of intracellular and/or extracellular ice formation, or even prevent such ice formation, by reducing the freezing point of water in the body fluid affected by the cryoprotectant. It is believed that after the cryoprotectant is absorbed into the epidermis and/or dermis, the cryoprotectant dissolves in or otherwise combines with water of the intracellular and/or extracellular fluid to delay the onset of ice formation by lowering the freezing point of the solution in which it resides. For example, the cryoprotectant may reduce the freezing point of the body fluid from, e.g., about −2° C. to about −5° C., −10° C., −16° C., or other temperatures suitable for a particular treatment. In some embodiments, the cryoprotectant may have a sufficient concentration in the body fluid such that water in the body fluid does not freeze but instead vitrifies under low temperature conditions. As a result, the onset of intracellular and/or extracellular ice formation may be prevented in these embodiments.

One expected advantage of several of the embodiments of the method 80 is that an operator may use lower treatment temperatures for selectively affecting lipid-rich cells of the subject without causing freezing damage to the epidermis and/or dermis of the subject. The applied cryoprotectant may lower the freezing point of the skin of the subject or body fluid in the target region to at least reduce the risk of intracellular and/or extracellular ice formation at such low treatment temperatures.

Another expected advantage is that the epidermis and/or dermis of the subject may be continually protected against freezing damage. It is believed that a topically administered cryoprotectant may protect the treatment region of the skin of the subject. After the cryoprotectant is applied to the skin of the subject, the cryoprotectant is believed to enter the epidermis, the dermis, and eventually the blood stream of the subject. The subject's blood stream then may carry the cryoprotectant away from the treatment region. As a result, the cryoprotectant concentration in the treatment region drops, and the freezing point of the subject's affected body fluid increases to heighten the risk of freezing damage. Accordingly, continually supplying the cryoprotectant to the skin of the subject may at least reduce or even prevent such a risk.

Another expected advantage of several of the embodiments is that cooling the skin of the subject may increase the residence time of the cryoprotectant and may reduce local and/or systemic side effects of the cryoprotectant. It is believed that the skin of the subject absorbs the cryoprotectant at a slower rate under low temperature conditions than under normal temperature (e.g., body temperature) conditions. Thus, the reduced absorption rate may increase the amount of time it takes for the subject's blood stream to remove the cryoprotectant, and thus prolong the efficacy of the cryoprotectant. It is also believed that certain cryoprotectants at certain concentration levels may be toxic to the subject by causing, for example, denaturation of proteins (e.g., enzymes). Thus, reducing the absorption rate of the cryoprotectant may reduce the cryoprotectant concentration in deeper tissues, and thus may reduce the associated local or systemic side effects.

F. CRYOPROTECTANTS

A cryoprotectant suitable to be used in the treatment system 100 of FIG. 1 is a substance that may protect biological tissues of a subject from freezing damage (e.g., damage due to ice formation). The cryoprotectant may contain a temperature depressant along with a thickening agent, a pH buffer, a humectant, a surfactant, and/or other additives. The cryoprotectant may be formulated as a liquid (e.g., an aqueous solution or a non-aqueous solution), a gel, a hydrogel, or a paste. The cryoprotectant may be hygroscopic, thermally conductive, and is ideally biocompatible. In certain embodiments, the cryoprotectant may be formulated to be ultrasonically acoustic to allow ultrasound to pass through the cryoprotectant, such as a water-based gel described in U.S. Pat. No. 4,002,221 issued to Buchalter and U.S. Pat. No. 4,459,854 issued to Richardson et al., the entire disclosures of which are incorporated herein by reference.

The temperature depressant may include polypropylene glycol (PPG), polyethylene glycol (PEG), propylene glycol, ethylene glycol, dimethyl sulfoxide (DMSO), or other glycols. The temperature depressant may also include ethanol, propanol, iso-propanol, butanol, and/or other suitable alcohol compounds. The temperature depressant may lower the freezing point of a solution (e.g., body fluid) to about 0° C. to −40° C., and more preferably to about −10° C. to −16° C. Certain temperature depressants (e.g., PPG, PEG, etc.) may also be used to improve smoothness of the cryoprotectant and to provide lubrication.

The thickening agent may include carboxyl polyethylene polymer, hydroxyethyl xylose polymer, and/or other viscosity modifiers to provide a viscosity in the range of about 1 cP to about 10,000 cP, more preferably in the range of about 4,000 cP to about 8,000 cP, and most preferably from about 5,000 cP to about 7,000 cP. The cryoprotectant with a viscosity in this range may readily adhere to the treatment device, the skin of the subject, and/or the interface between the treatment device and the skin of the subject during treatment.

The pH buffer may include cholamine chloride, cetamidoglycine, tricine, glycinamide, bicine, and/or other suitable pH buffers. The pH buffer may help the cryoprotectant to have a consistent pH of about 3.5 to about 11.5, more preferably about 5 to about 9.5, and most preferably about 6 to about 7.5. In certain embodiments, the pH of the cryoprotectant may be close to the pH of the skin of the subject.

The humectant may include glycerin, alkylene glycol, polyalkylene glycol, propylene glycol, glyceryl triacetate, polyols (e.g., sorbitol and/or maltitol), polymeric polyols (e.g., polydextrose), quillaia, lactic acid, and/or urea. The humectant may promote the retention of water to prevent the cryoprotectant from drying out.

The surfactant may include sodium dodecyl sulfate, ammonium lauryl sulfate, sodium lauryl sulfate, alkyl benzene sulfonate, sodium lauryl ether sulfate, and other suitable surfactants. The surfactant may promote easy spreading of the cryoprotectant when an operator applies the cryoprotectant to the treatment device, the skin of the subject, and/or the interface between the treatment device and the skin of the subject during treatment.

The cryoprotectant may also include other additives in addition to or in lieu of the ingredients described above. For example, the cryoprotectant may also include a coloring agent, perfume, emulsifier, an anesthetic agent, and/or other ingredient.

In a particular embodiment, the cryoprotectant may include about 30% polypropylene glycol, about 30% glycerin, and about 40% ethanol. In another embodiment, the cryoprotectant may include about 40% propylene glycol, about 0.8% hydroxyethylcellulose, and about 59.2% water. In a further embodiment, the cryoprotectant may include about 50% polypropylene glycol, about 40% glycerin, and about 10% ethanol.

G. TREATMENT DEVICES WITH ROTATABLE HEAT EXCHANGING ELEMENTS

Figure 7:
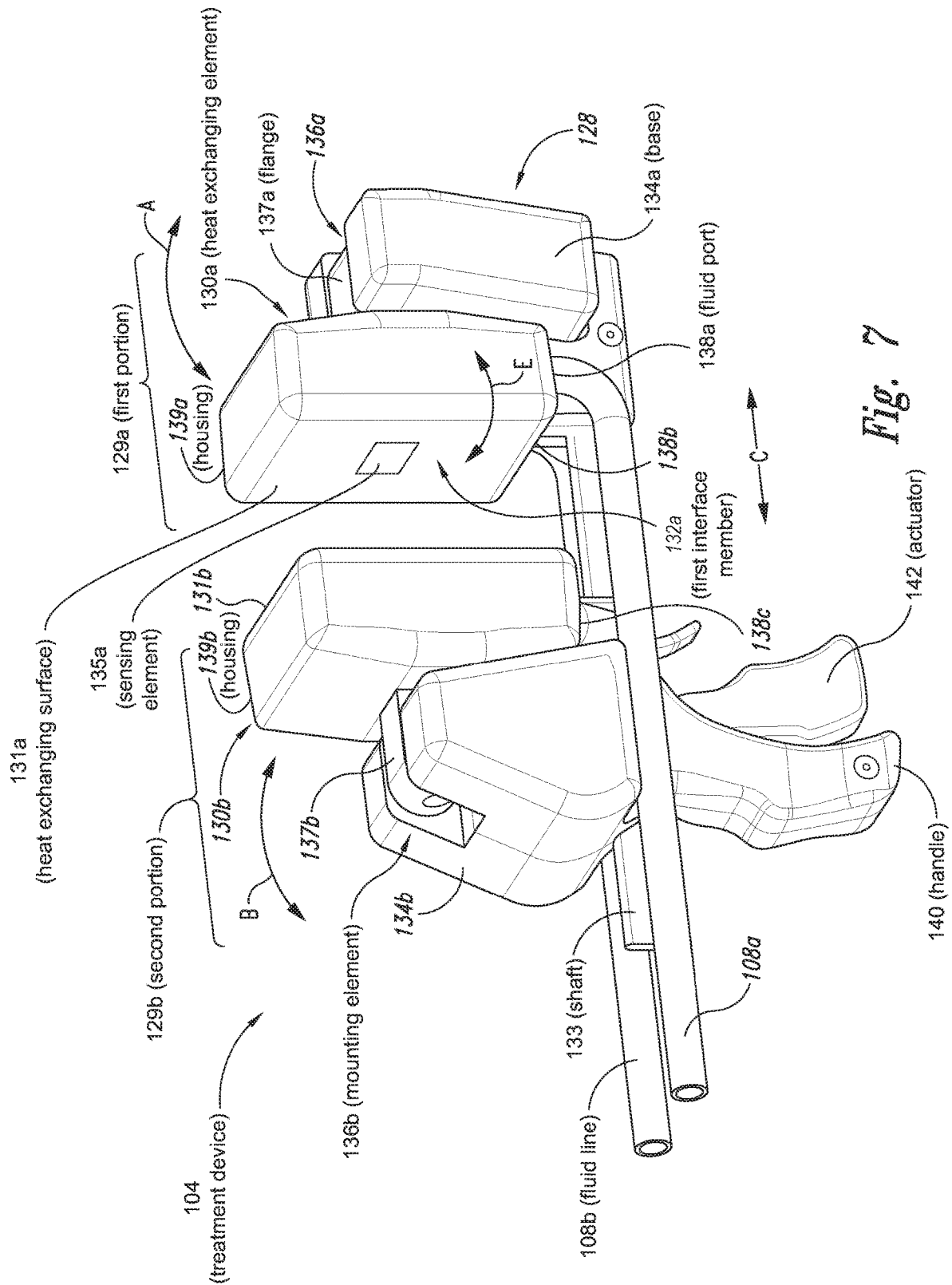
FIG. 7 is an isometric view of a treatment device for removing heat from subcutaneous lipid-rich cells in accordance with an embodiment of the invention.

FIG. 7 is an isometric view of a treatment device 104 in accordance with one embodiment of the invention suitable for use in the treatment system 100. In this embodiment, the treatment device 104 includes a support 128 having a first portion 129a and a second portion 129b, a first heat exchanging element 130a located at the first portion 129a, and a second heat exchanging element 130b located at the second portion 129b. The treatment device 104 is generally configured to be a handheld unit for manual operation, and/or it may be strapped or otherwise configured to be releasably attached to the subject. The first heat exchanging element 130a and/or the second heat exchanging element 130b may be configured to move along the support 128 and/or rotate to position the heat exchanging elements 130a-b for applying pressure to the treatment region during operation.

The first and second heat exchanging elements 130a-b may have many similar features. As such, the features of the first heat exchanging element 130a are described below with reference symbols followed by an "a", and corresponding features of the second heat exchanging element 130b are shown and noted by the same reference symbol followed by a "b." The first heat exchanging element 130a may include a housing 139a and fluid ports 138a-b coupled to the fluid lines 108a-b. The housing 139a may be constructed from polymeric materials, metals, ceramics, woods, and/or other suitable materials. The housing 139a shown in FIG. 7 is generally rectangular, but it may have any other desired shape.

The first heat exchanging element 130a may further include a first interface member 132a having a first heat exchanging surface 131a for transferring heat to/from the subject 101. A cryoprotectant (not shown) may be applied to the heat exchanging surface 131a to prevent ice from forming thereon when the temperature is reduced to a temperature around or below the freezing point of water (0° C.). In one embodiment, the first heat exchanging surface 131a is generally planar, but in other embodiments, the first heat exchanging surface 131a is non-planar (e.g., curved, faceted, etc.) The first interface member 132a may be constructed from any suitable material with a thermal conductivity greater than 0.05 Watts/Meter ° Kelvin, and in many embodiments, the thermal conductivity is more than 0.1 Watts/Meter ° Kelvin. Examples of suitable materials include aluminum, other metals, metal alloys, graphite, ceramics, some polymeric materials, composites, or fluids contained in a flexible membrane. Portions of the first heat exchanging surface 131a may be an insulating material with a thermal conductivity less than 0.05 Watts/Meter ° Kelvin.

The first heat exchanging element 130a may also include at least one sensing element 135a proximate to the first heat exchanging surface 131a. The sensing element 135a, for example, may be generally flush with the heat exchanging surface 131a. Alternatively, it may be recessed or protrude from the surface. The sensing element 135a may include a temperature sensor, a pressure sensor, a transmissivity sensor, a bio-resistance sensor, an ultrasound sensor, an optical sensor, an infrared sensor, a sensor for measuring blood flow, or any other desired sensor. In one embodiment, the sensing element 135a may be a temperature sensor configured to measure the temperature of the first heat exchanging surface 131a and/or the temperature of the skin of the subject. For example, the temperature sensor may be configured as a probe or as a needle that penetrates the skin during measurement. Examples of suitable temperature sensors include thermocouples, resistance temperature devices, thermistors (e.g., neutron-transmutation-doped germanium thermistors), and infrared radiation temperature sensors. In another embodiment, the sensing element 135a may be an ultrasound sensor configured to measure the thickness of a fat layer in the subject or crystallization of subcutaneous fat in the treatment region of a subject. In yet another embodiment, the sensing element 135a may be an optical or infrared sensor configured to monitor an image of the treatment region to detect, for example, epidermal physiological reactions to the treatment. In yet another embodiment, the sensing element 135a may be a device to measure blood flow. The sensing element 135a may be in electrical communication with the processing unit 114 via, for example, a direct wired connection, a networked connection, and/or a wireless connection.

The treatment device 104 may further include a mounting element 136a that couples the first heat exchanging element 130a to the first portion 129a of the support 128. The mounting element 136a, for example, may be a pin, a ball joint, a bearing, or other types of rotatable joints. Suitable bearings include, but are not limited to, ball bearings, roller bearings, thrust bearings, and journal bearings. The mounting element 136a may accordingly be configured to rotatably couple the first heat exchanging element 130a to the support 128. In certain embodiments, the first heat exchanging element 130a may rotate relative to the support 128 in two dimensions (indicated by arrow A) such that the angle between the first and second heat exchanging surfaces 131a-b may be adjusted. In another embodiment, the first heat exchanging element 130a may rotate in three dimensions relative to the support 128 (as indicated by arrows A and B).

A specific embodiment of the mounting element 136a includes a first mounting base 134a and a flange 137a coupled to the base 134a by a rotatable or pivotable joint. By rotatably mounting at least one of the first and second heat exchanging elements 130a-b to the support 128, the angle between the first and second heat exchanging surfaces 131a-b may be adjusted. For example, the first and second heat exchanging elements 130a-b may be generally parallel to each other, i.e., have an angle of generally 0° between the first and second heat exchanging surfaces 131a-b. The first and second heat exchanging elements 130a-b may also be generally co-planar, i.e., have an angle of generally 180° between the first and second heat exchanging surfaces 131a-b. With the rotatable mounting elements 136a-b, any angle of about 0° to about 180° between the first and second heat exchanging surfaces 131a-b may be achieved.

The treatment device 104 may further include a shaft 133, and the first mounting base 134a may be attached to the shaft 133. As explained in more detail below, at least one of the heat exchanging elements 130a-b moves along the shaft 133 and/or the shaft 133 moves relative to the support 128 to adjust the distance between the first and second heat exchanging elements 130a-b (shown by arrow C). The shaft 133, more specifically, extends between the first and second heat exchanging elements 130a-b to enable movement of at least one of the heat exchanging elements 130a-b relative to the support 128. In certain embodiments, the first mounting base 134a may be fixedly attached to the shaft 133, and a second mounting base 134b of the second heat exchanging element 130b is configured such that the second mounting base 134b may slide along the shaft 133. In other embodiments, both the first mounting base 134a and the second mounting base 134b may be configured to slide along the shaft 133. The shaft 133 is generally constructed from polymeric materials, metals, ceramics, woods, or other suitable materials.

The treatment device 104 further includes a handle 140 slidably coupled to the shaft 133 or formed as a part of the shaft 133. The handle 140 is configured to be held by a hand of an operator. For example, the handle 140 may have a grip with grooves to improve stability of the treatment device 104 when held by the operator. The handle 140 further includes an actuator 142 that operates with the shaft 133 to move the second heat exchanging element 130b relative to the shaft 133. The actuator 142 may be a lever that engages the shaft 133 to incrementally advance the second heat exchanging element 130b in an axial motion (arrow C) along the shaft 133.

In operation, an operator may hold the treatment device 104 in one hand by grasping the handle 140. Then, the heat exchanging elements 130a-b may be rotated via the mounting elements 136a-b to achieve a desired orientation. The operator may place the treatment device 104 having the heat exchanging elements 130a-b in the desired orientation proximate to the skin of the subject to remove heat from a subcutaneous region of the subject 101. In one embodiment, the operator may clamp a portion of the skin of the subject between the heat exchanging surfaces 131a-b when the surfaces 131a-b are generally parallel to each other. In another embodiment, the operator may press the heat exchanging surfaces 131a-b against the skin of the subject when the surfaces 131a-b are generally co-planar. In certain embodiments, the operator may use thermoelectric coolers to remove heat from the subcutaneous region as described below with reference to FIG. 8. The operator may also monitor and control the treatment process by collecting measurements, such as skin temperatures, from the sensing element 135a. By cooling the subcutaneous tissues to a temperature lower than 37° C., subcutaneous lipid-rich cells may be selectively affected. The affected cells are then reabsorbed into the subject through natural processes.

One expected advantage of using the treatment device 104 is that the treatment device may be applied to various regions of the subject's body because the two heat exchanging elements 130a-b may be adjusted to conform to any body contour. Another expected advantage is that by pressing the treatment device 104 against the skin of the subject, blood flow through the treatment region may be reduced to achieve efficient cooling. Yet another expected advantage is that by applying the cryoprotectant to prevent icing and to allow pre-cooling of the heat exchanging elements, the treatment duration may be shortened. Yet another expected advantage is that maintaining the temperature of the heat exchanging elements may reduce the power consumption of the device. Still another expected advantage is that the power requirement is reduced for each of the heat exchanging elements 130a-b because heat is removed from the skin through the two heat exchanging surfaces 131a-b instead of a single heat exchanging element.

The first and second heat exchanging elements 130a-b may have many additional embodiments with different and/or additional features without detracting from the operation of both elements. For example, the second heat exchanging element 130b may or may not have a sensing element proximate to the second heat exchanging surface 131b. The second heat exchanging element 130b may be constructed from a material that is different from that of the first heat exchanging element 130a. The second mounting base 134b may have a shape and/or a surface configuration different from that of the first mounting base 134a. The first heat exchanging element 130a may be rotatable, but the second heat exchanging element 130b may be non-rotatable.

The first and second heat exchanging elements 130a-b may further include a thermoelectric cooler (not shown), such as a Peltier-type element, proximate to the interface members 132a-b. The thermoelectric cooler may be a single Peltier-type element or an array of Peltier-type elements. One suitable thermoelectric cooler is a Peltier-type heat exchanging element (model # CP-2895) produced by TE Technologies, Inc. in Traverse City, Michigan.

H. TREATMENT DEVICE HAVING A PLURALITY OF COOLING ELEMENTS

Figure 8A:
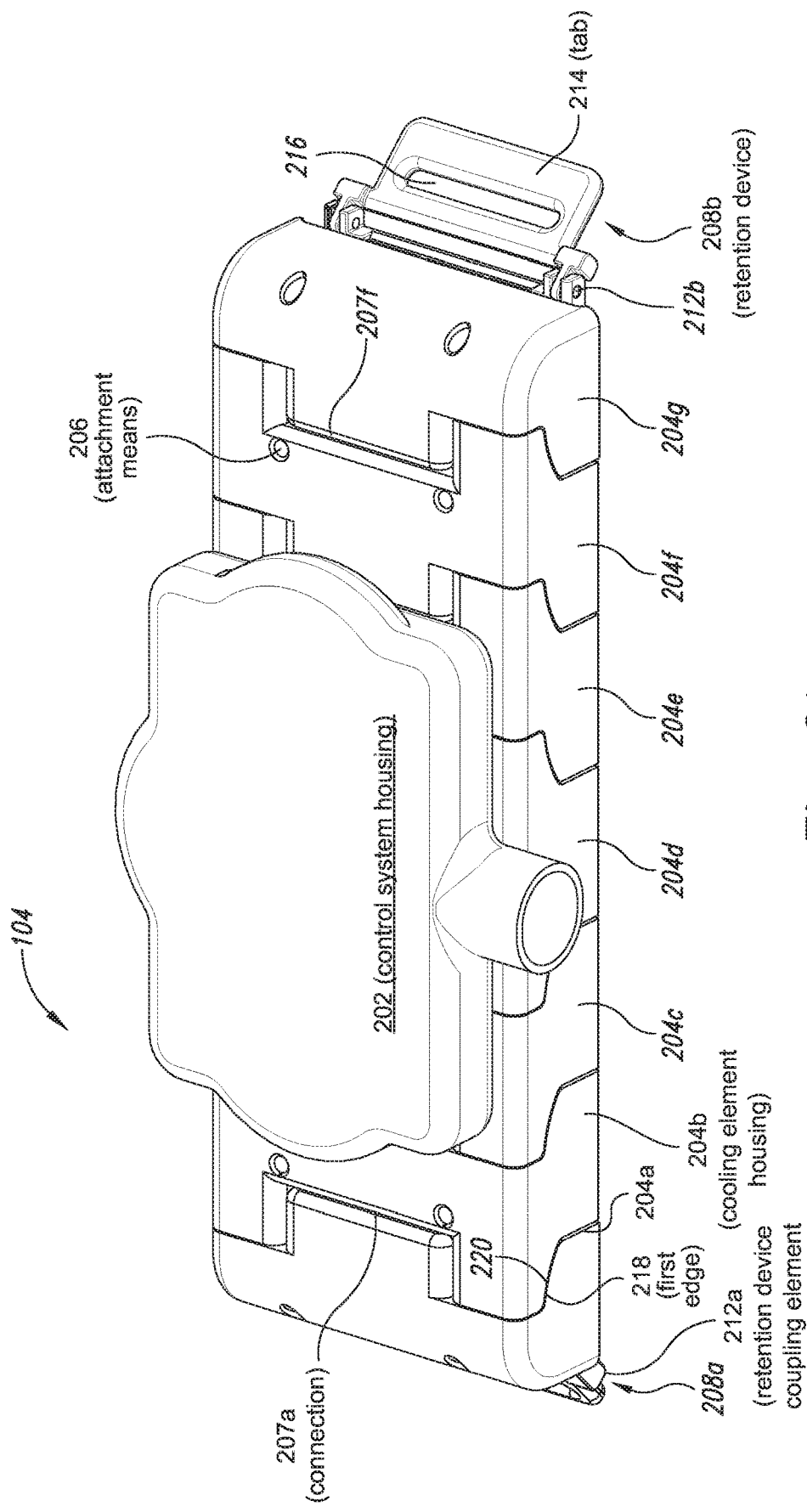
FIGS. 8A-B are isometric views of a treatment device for removing heat from subcutaneous lipid-rich cells in accordance with a further embodiment of the invention.
Figure 8B:
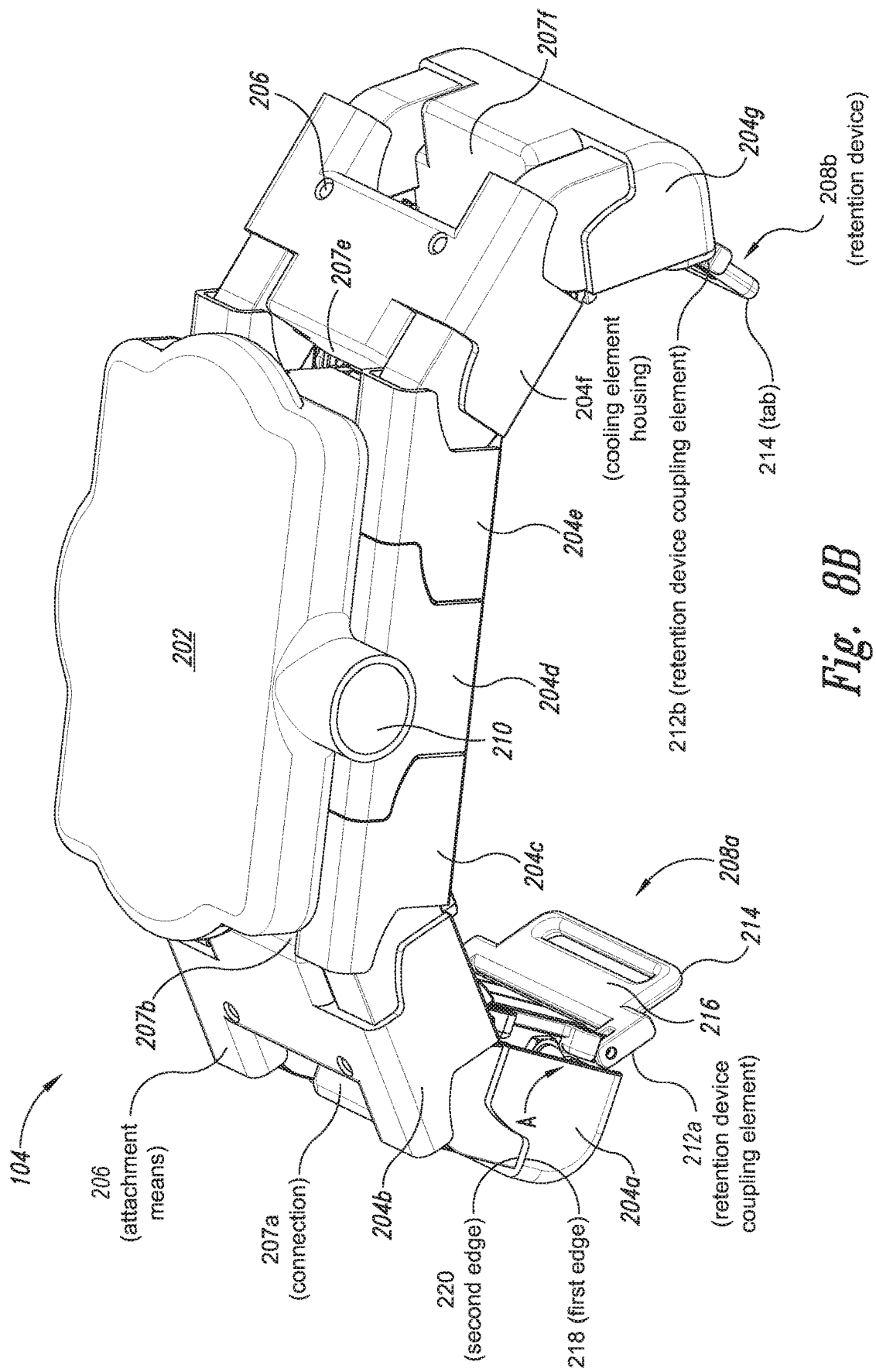

FIGS. 8A-B are isometric views of a treatment device 104 in accordance with embodiments of the invention suitable for use in the treatment system 100. In this embodiment, the treatment device 104 includes a control system housing 202 and cooling element housings 204a-g. The cooling element housings 204a-g are connected to the heat exchanging elements (not shown) by attachment means 206. The attachment means may be any mechanical attachment device such as a screw or pin as is known in the art. The plurality of cooling element housings 204a-g may have many similar features. As such, the features of the first cooling element housing 204a are described below with reference symbols followed by an "a," corresponding features of the second cooling element housing 204b are shown and noted by the same reference symbol followed by a "b," and so forth. The cooling element housing 204a may be constructed from polymeric materials, metals, ceramics, woods, and/or other suitable materials. The cooling element housing 204a shown in FIGS. 8A-B is generally rectangular, but it may have any other desired shape.

The treatment device 104 is shown in a first relatively flat configuration in FIG. 8A and in a second curved configuration in FIG. 8B. As shown in FIG. 8B, each segment of the cooling element housings 204a-g is rotatably connected to adjacent segments and moveable about connection 207a-f to allow the treatment device 104 to curve. The connection 207a-f, for example, may be a pin, a ball joint, a bearing, or other type of rotatable joints. The connection 207 may accordingly be configured to rotatably couple the first cooling element housing 204a to the second cooling element housing 204b. According to aspects of the invention, the first cooling element housing 204a may rotate relative to the second cooling element housing 204b (indicated by arrow A), each adjacent moveable pair of cooling elements being such that, for example, the angle between the first and second cooling element housings 204a and 204b may be adjusted up to 45°. In this way, the treatment device is articulated such that it may assume a curved configuration as shown in FIG. 8B, conformable to the skin of a subject.

One advantage of the plurality of rotatable heat exchanging surfaces is that the arcuate shape of the treatment device may concentrate the heat transfer in the subcutaneous region. For example, when heat exchanging surfaces are rotated about a body contour of a subject, the arcuate shape may concentrate heat removal from the skin.

The control system housing 202 may house a processing unit for controlling the treatment device 104 and/or fluid lines 108a-b and/or electrical power and communication lines. The control system housing 202 includes a harness port 210 for electrical and supply fluid lines (not shown for purposes of clarity). The control system housing 202 may further be configured to serve as a handle for a user of the treatment device 104. Alternatively, the processing unit may be contained at a location other than on the treatment device.

The treatment device 104 may further include at each end of the treatment device 104 retention devices 208a and 208b. The retention devices 208a and 208b are rotatably connected to a frame by retention device coupling elements 212a-b. The retention device coupling elements 212a-b, for example, may be a pin, a ball joint, a bearing, or other type of rotatable joints. In certain embodiments, the retention devices 208a and 208b may be rigidly affixed to the end portions of the cooling element housings 204a and 204g. Alternately, the retention device may attach to control system housing 202.

The retention devices 208a and 208b are each shown as tabs 214, each having a slot 216 therein for receiving a band or elastomeric strap (not shown for purposes of clarity) to retain the treatment device 104 in place on a subject 101 during treatment. Alternatively, the treatment device may not contain any attached retention device and may be held in place by hand, may be held in place by gravity, or may be held in place with a band, elastomeric strap, or non-elastic fabric (e.g., nylon webbing) wrapped around the treatment device 104 and the subject 101.

As shown in FIGS. 8A-B, the cooling element housings 204a-g have a first edge 218 and an adjacent second edge 220 of a reciprocal shape to allow the treatment device 104 to mate and, thus, configure in a flat configuration. The first edge 218 and the second edge 220 are generally angular in the Figures; however, the shape could be curved, straight, or a combination of angles, curves, and straight edges that provides a reciprocal shape between adjacent segments of the cooling element housings 204a-g.

I. ADDITIONAL EMBODIMENTS OF TREATMENT DEVICE

Figure 9:
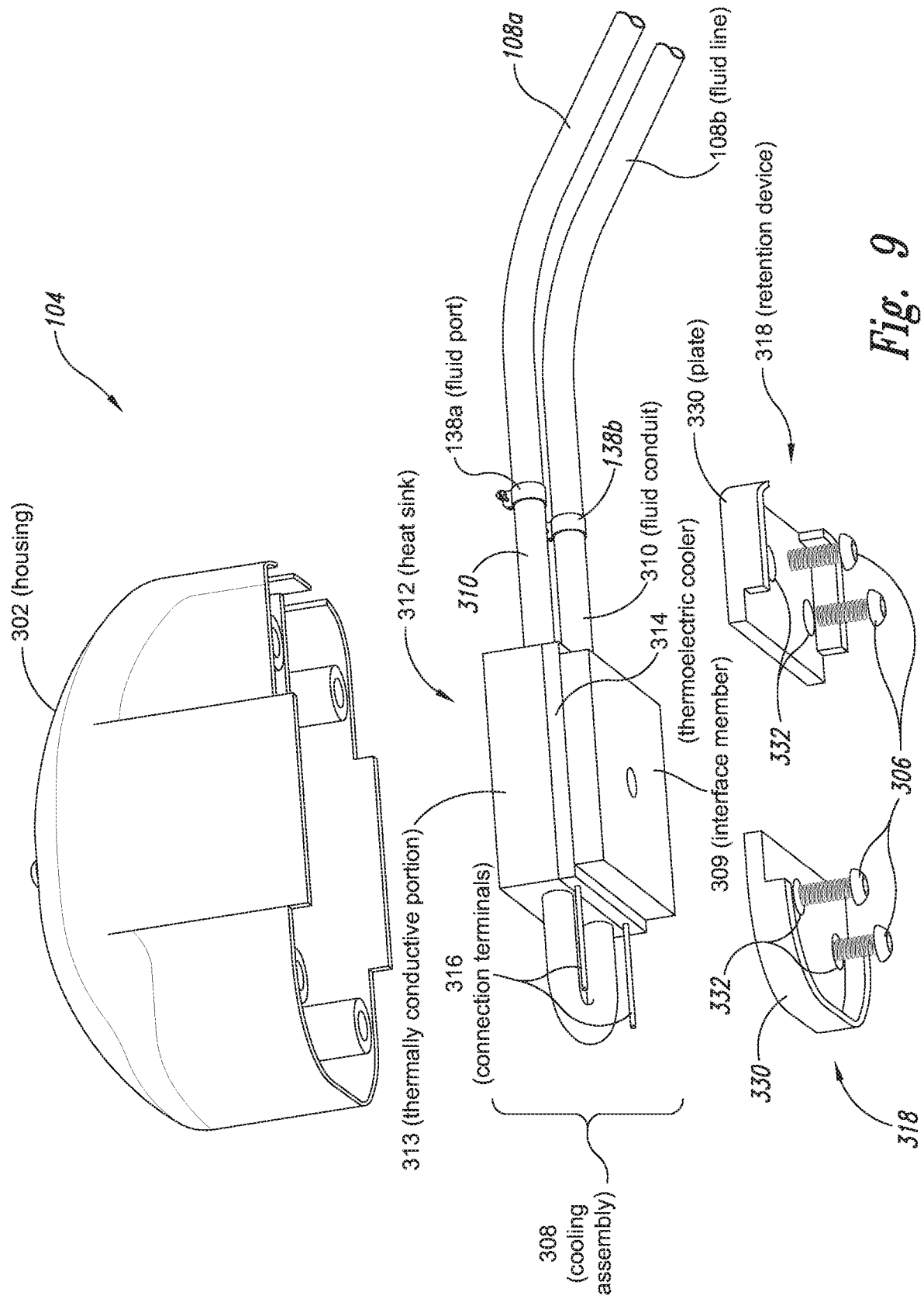
FIG. 9 is an isometric and exploded view of a treatment device for removing heat from subcutaneous lipid-rich cells in accordance with a further embodiment of the invention.

FIG. 9 is an isometric and exploded view of a treatment device 104 in accordance with another embodiment of the invention. The treatment device 104 may include a housing 302, a cooling assembly 308 at least partially disposed in the housing 302, and retention devices 318 configured for fastening the cooling assembly 308 to the housing 302. The treatment device 104 may also include a vibration member disposed in the housing 302, as described in more detail below with reference to FIG. 10.

The cooling assembly 308 may include a heat sink 312, a thermally conductive interface member 309, and a thermoelectric cooler 314 disposed between the heat sink 312 and the interface member 309. The thermoelectric cooler 314 may be connected to an external power supply (not shown) via connection terminals 316. In the illustrated embodiment, the heat sink 312 includes a U-shaped fluid conduit 310 at least partially embedded in a thermally conductive portion 313 of the heat sink 312. The fluid conduit 310 includes fluid ports 138a-b that may be coupled to a circulating fluid source (not shown) via the fluid lines 108a-b. In other embodiments, the heat sink 312 may include a plate-type heat exchanger, a tube and shell heat exchanger, and/or other types of heat exchanging device. The interface member 309 may include a plate constructed from a metal, a metal alloy, and/or other types of thermally conductive material. The thermoelectric cooler 314 may be a single Peltier-type element or an array of Peltier-type elements. One suitable thermoelectric cooler is a Peltier-type heat exchanging element (model # CP-2895) produced by TE Technology, Inc. in Traverse City, Michigan.

Individual retention devices 318 may include a plate 330 and a plurality of fasteners 306 extending through a plurality of apertures 332 (two are shown for illustrative purposes) of the plate 330. In the illustrated embodiment, the fasteners 306 are screws that may be received by the housing 302. In other embodiments, the fasteners 306 may include bolts, clamps, clips, nails, pins, rings, rivets, straps, and/or other suitable fasteners. During assembly, the cooling assembly 308 is first at least partially disposed in the internal space 303 of the housing 302. Then, the retention devices 318 are positioned proximate to the cooling assembly 308, and the fasteners 306 are extended through the apertures 332 of the plate 330 to engage the housing 302. The fasteners 306, the plates 330, and the housing 302 cooperate to hold the cooling assembly 308 together.

By applying power to the thermoelectric cooler 314, heat may be effectively removed from the skin of the subject to a circulating fluid in the fluid conduit 310. For example, applying a current to the thermoelectric cooler 314 may achieve a temperature generally below 37° C. on the first side 315a of the thermoelectric cooler 314 to remove heat from the subject via the interface member 309. The thermoelectric cooler 314 transfers the heat from the first side 315a to the second side 315b. The heat is then transferred to the circulating fluid in the fluid conduit 310.

Figure 10:
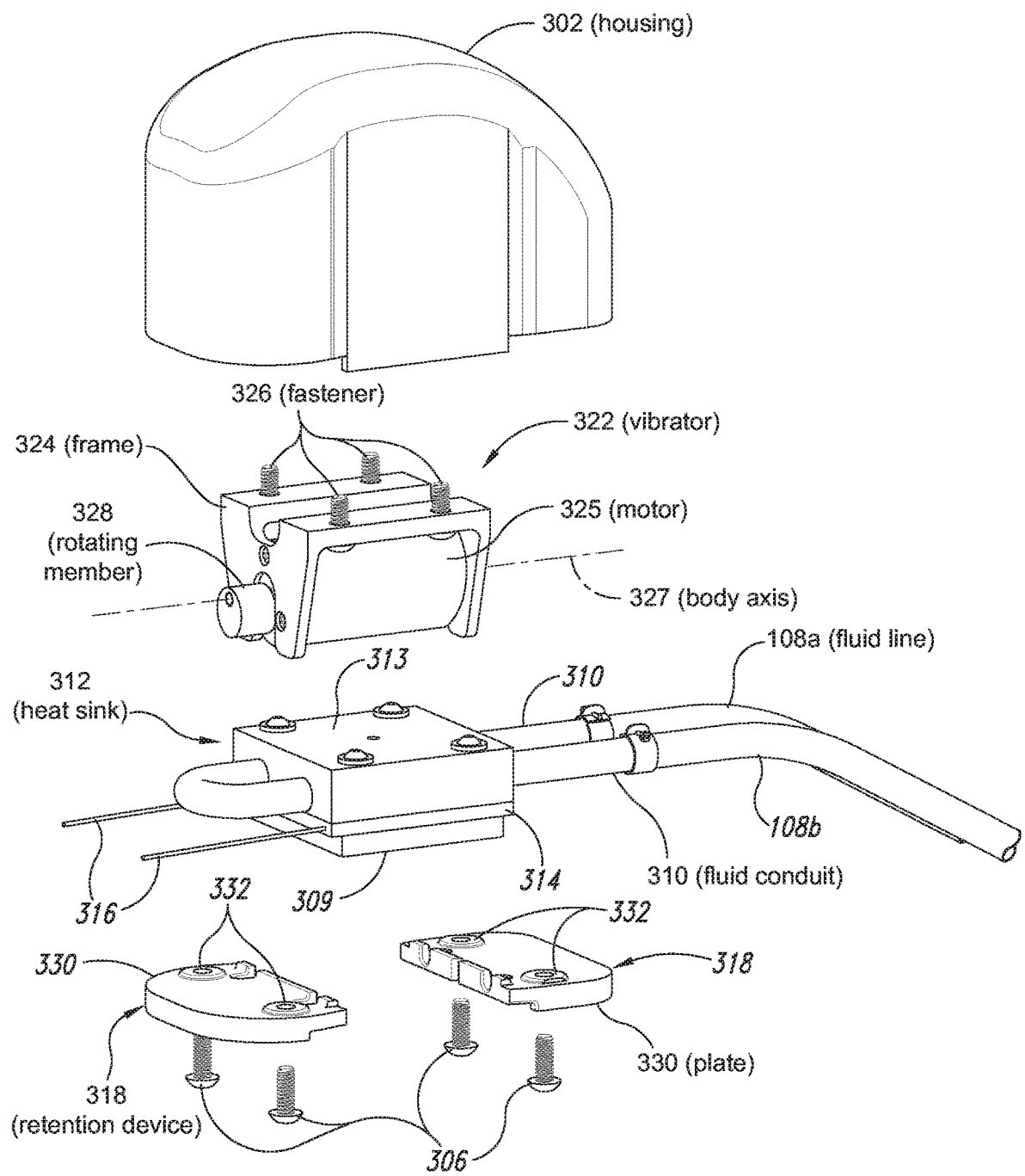
FIG. 10 is an isometric and exploded view of a vibrator disposed in the treatment device for removing heat from subcutaneous lipid-rich cells in accordance with yet another embodiment of the invention.

FIG. 10 is an isometric and exploded view of a vibrator 322 disposed in the treatment device 104 of FIG. 9. The vibrator 322 may include a frame 324, a motor 325 carried by the frame 324, a rotating member 328 operatively coupled to the motor 325, and a plurality of fasteners 326 (e.g., screws) for fixedly attaching the frame 324 to the housing 302. In the illustrated embodiment, the motor 325 has an output shaft (not shown) generally centered about a body axis 327 of the motor 325. One suitable motor is a direct current motor (model # Pittman 8322S008-R1) manufactured by Ametek, Inc., of Harleysville, Pa. The rotating member 328 has a generally cylindrical shape and is off-centered from the body axis 327. In other embodiments, the motor 325 may have an off-centered shaft that is operatively coupled to the rotating member 328.

In operation, applying electricity to the motor 325 may cause the rotating member 328 to rotate around the body axis 327 of the motor 325. The off-centered rotating member 328 causes the vibrator 322 to be off-balanced about the body axis 327, and vibration in the frame 324 and the housing 302 may result.

The disclosures of U.S. patent application Ser. No. 11/741,271, U.S. patent application Ser. No. 11/750,953, and U.S. Provisional Application No. 60/795,799, are incorporated herein by reference in their entireties.

J. EXAMPLES

The applicants conducted experiments to cool subcutaneous lipid-rich cells in a pig using a treatment device as shown in FIG. 9 and a cryoprotectant. A first cryoprotectant composition used in the experiments included about 30% polypropylene glycol, about 30% glycerin, and about 40% ethanol (cryoprotectant I). A second cryoprotectant composition used in the experiments included about 40% propylene glycol, about 0.8% hydroxyethylcellulose, and about 59.2% water (cryoprotectant II). Skin surface temperatures investigated include −11° C., −12° C., −14° C., −16° C., and −20° C.

Each testing site was cleaned and shaved, and a surface thermocouple was placed on the skin of the pig to control the treatment device. A number of 3"×3" squares of Webril® Undercast Padding #3175, supplied by Tyco Healthcare of Mansfield Mass. ("Webril"), were soaked with 8 milliliters of either cryoprotectant I or cryoprotectant II. The soaked Webril squares were then placed on the test sites for 5 minutes, and the treatment device was then applied to the Webril squares to achieve a desired surface temperature. Once the desired surface temperature was achieved, the surface temperature was maintained for a treatment period of up to about 30 minutes. After the treatment period, the skin of the pig was inspected for freezing.

The results of several experiments indicate that both cryoprotectant I and cryoprotectant II significantly lowered the freezing point of the skin of the pig. In particular, when the surface temperature was between about −12° C. to about −16° C., limited or no skin freezing was observed.

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number, respectively. When the claims use the word "or" in reference to a list of two or more items, that word covers all of the following interpretations of the word: any of the items in the list, all of the items in the list, and any combination of the items in the list.

The above detailed descriptions of embodiments of the invention are not intended to be exhaustive or to limit the invention to the precise form disclosed above. While specific embodiments of, and examples for, the invention are described above for illustrative purposes, various equivalent modifications are possible within the scope of the invention, as those skilled in the relevant art may recognize. For example, while steps are presented in a given order, alternative embodiments may perform steps in a different order. The various embodiments described herein may be combined to provide further embodiments.

In general, the terms used in the following claims should not be construed to limit the invention to the specific embodiments disclosed in the specification, unless the above detailed description explicitly defines such terms. While certain aspects of the invention are presented below in certain claim forms, the inventors contemplate the various aspects of the invention in any number of claim forms. Accordingly, the inventors reserve the right to add additional claims after filing the application to pursue such additional claim forms for other aspects of the invention.

We claim:

1. A system for selectively destroying subcutaneous lipid rich cells of a target region of a subject with skin, comprising:
   a thermoelectric treatment device having
      a fluid-cooled heat-exchanger,
      a thermoelectric cooler having a backside substantially covered by the fluid-cooled heat-exchanger,
      a heat exchanging element having a first side in thermal communication with a heat exchanging surface and a second side opposite the first side in thermal communication with a front side of the thermoelectric cooler, the heat exchanging element being configured to reduce a temperature of the target region for up to about 30 minutes such that lipid rich cells in the region are affected while preserving non-lipid rich cells proximate to the heat exchanging surface;
      a housing having an opening configured to receive the fluid-cooled heat-exchanger and thermoelectric cooler such that a sidewall of housing surrounds the fluid-cooled heat-exchanger and thermoelectric cooler;
   at least one fluid line extending though an opening in the housing and in fluid communication with the fluid-cooled heat-exchanger, and
   an absorbent configured to be positioned at least partially between the heat exchanging surface and the subject's skin and is configured to be thermally coupled to the treatment device, the absorbent being preloaded with an excess of cryoprotectant to continually supply the excess of cryoprotectant from the absorbent to the subject's skin during the up to about 30 minutes the temperature of the target region is reduced, wherein the cryoprotectant comprises about 40% propylene glycol and further comprises about 0.8% hydroxyethylcellulose.

2. The system of claim 1, wherein the heat exchanging element reaches a temperature of about −20° C.

3. The system of claim 1, wherein the absorbent is a cotton pad or a gauze to continually supply the cryoprotectant.

4. The system of claim 1, wherein the cryoprotectant includes a viscosity that is in the range of about 1 cP to about 4,000 cP.

5. The system of claim 1, wherein the absorbent is configured to substantially cover an interface between the treatment device and the skin, wherein the absorbent is configured to contact at least one of the treatment device and the skin.

6. The system of claim 5, wherein the cryoprotectant further comprises a pH buffer to maintain the pH in the range of about 3 to about 11.

7. The system of claim 5, wherein the cryoprotectant is water-soluble.

8. The system of claim 5, wherein the cryoprotectant includes a viscosity in the range of about 1 cP to about 10,000 cP.

9. The system of claim 5, wherein the cryoprotectant has a freezing point below about −10° C.

10. The system of claim 1, wherein the excess of cryoprotectant preloaded onto the absorbent is configured to continually supply the cryoprotectant from the absorbent to the subject's skin during the up to about 30 minutes the temperature of the target region is reduced in light of absorption of the cryoprotectant by the skin.

11. The system of claim 1, wherein the cryoprotectant has a freezing point below about −20° C.

12. A system for removing heat from subcutaneous lipid rich cells of a target region of a subject having skin, comprising:
   a treatment device having a housing and a thermal mass in thermal communication with a heat exchanging surface, the thermal mass being configured to reduce a temperature of the target region for up to about 30 minutes such that lipid rich cells in the target region are affected while preserving non-lipid rich cells proximate to the heat exchanging surface;
   an absorbent configured to be positioned at least partially between the heat exchanging surface and the subject's skin, the absorbent being preloaded with an excess of a cryoprotectant to continually supply the excess of cryoprotectant from the absorbent to the subject's skin during the up to about 30 minutes the temperature of the target region is reduced, wherein the cryoprotectant comprises about 40% propylene glycol and further comprises 0.8% hydroxyethylcellulose.

13. The system of claim 12, wherein the absorbent is configured to substantially cover an interface between the treatment device and the skin, wherein the absorbent is configured to contact at least one of the treatment device and the skin.

14. The system of claim 13 wherein the cryoprotectant further comprises a pH buffer to maintain the pH in the range of about 3 to about 11.

15. The system of claim 13 wherein the cryoprotectant is water-soluble.

16. The system of claim 13 wherein the cryoprotectant includes a viscosity in the range of about 1 cP to about 10,000 cP.

17. The system of claim 13 wherein the cryoprotectant has a freezing point below about −10° C.

18. The system of claim 12, wherein the heat exchanging surface reaches a temperature of about −20° C.

19. The system of claim 12, wherein the absorbent is a cotton pad or a gauze to continually supply the cryoprotectant.

20. The system of claim 12, wherein the cryoprotectant includes a viscosity that is in the range of about 1 cP to about 4,000 cP.

21. The system of claim 12, wherein the cryoprotectant has a freezing point below about −20° C.

22. The system of claim 12, wherein the excess of cryoprotectant preloaded onto the absorbent is configured to continually supply the cryoprotectant from the absorbent to the subject's skin during the up to about 30 minutes the temperature of the target region is reduced in light of absorption of the cryoprotectant by the skin.

23. A system for selectively destroying subcutaneous lipid rich cells of a target region of a subject with skin, comprising:
 a thermoelectric treatment device comprising:
  a fluid-cooled heat-exchanger;
  a thermoelectric cooler having a backside substantially covered by the fluid-cooled heat-exchanger; and
  a heat exchanging element having a first side in thermal communication with a heat exchanging surface and a second side opposite the first side in thermal communication with a front side of the thermoelectric cooler, the heat exchanging element being configured to reduce a temperature of the target region for up to about 30 minutes such that lipid rich cells in the region are affected while preserving non-lipid rich cells proximate to the heat exchanging surface; and
 an absorbent configured to be positioned at least partially between the heat exchanging surface and the subject's skin and is configured to be thermally coupled to the thermoelectric treatment device, the absorbent being preloaded with an excess of cryoprotectant to continually supply the excess of cryoprotectant from the absorbent to the subject's skin during the up to about 30 minutes the temperature of the target region is reduced, wherein the cryoprotectant comprises about 40% propylene glycol and further comprises about 0.8% hydroxyethylcellulose.

24. A system for selectively destroying subcutaneous lipid rich cells of a target region of a subject with skin, comprising:
 a thermoelectric treatment device comprising a heat exchanging element having a first side in thermal communication with a heat exchanging surface and a second side opposite the first side in thermal communication with a thermoelectric cooler, the heat exchanging element being configured to reduce a temperature of the target region for up to about 30 minutes such that lipid rich cells in the region are affected while preserving non-lipid rich cells proximate to the heat exchanging surface; and
 an absorbent configured to be positioned at least partially between the heat exchanging surface and the subject's skin and is configured to be thermally coupled to the thermoelectric treatment device, the absorbent being preloaded with an excess of cryoprotectant to continually supply the excess of cryoprotectant from the absorbent to the subject's skin during the up to about 30 minutes the temperature of the target region is reduced, wherein the cryoprotectant comprises about 40% propylene glycol and further comprises about 0.8% hydroxyethylcellulose.

\* \* \* \* \*